United States Patent
Lossos et al.

(10) Patent No.: US 11,311,537 B2
(45) Date of Patent: Apr. 26, 2022

(54) DIAGNOSIS AND TREATMENT OF LYMPHOPROLIFERATIVE DISORDERS WITH PARP INHIBITORS

(71) Applicant: UNIVERSITY OF MIAMI, Miami, FL (US)

(72) Inventors: Izidore Lossos, Miami, FL (US); Ramiro E. Verdun, Miami, FL (US)

(73) Assignee: UNIVERSITY OF MIAMI, Miami, FL (US)

( * ) Notice: Subject to any disclaimer, the term of this patent is extended or adjusted under 35 U.S.C. 154(b) by 102 days.

(21) Appl. No.: 16/345,624

(22) PCT Filed: Oct. 26, 2017

(86) PCT No.: PCT/US2017/058557
§ 371 (c)(1),
(2) Date: Apr. 26, 2019

(87) PCT Pub. No.: WO2018/081438
PCT Pub. Date: May 3, 2018

(65) Prior Publication Data
US 2020/0022979 A1    Jan. 23, 2020

Related U.S. Application Data

(60) Provisional application No. 62/413,812, filed on Oct. 27, 2016.

(51) Int. Cl.
| | | |
|---|---|---|
| *A61K 31/502* | (2006.01) | |
| *A61K 31/704* | (2006.01) | |
| *A61P 35/00* | (2006.01) | |
| *A61P 35/02* | (2006.01) | |
| *C12Q 1/6886* | (2018.01) | |
| *G01N 33/574* | (2006.01) | |

(52) U.S. Cl.
CPC .......... *A61K 31/502* (2013.01); *A61K 31/704* (2013.01); *A61P 35/00* (2018.01); *A61P 35/02* (2018.01); *C12Q 1/6886* (2013.01); *G01N 33/5748* (2013.01); *C12Q 2600/106* (2013.01); *C12Q 2600/158* (2013.01)

(58) Field of Classification Search
CPC ..... A61K 31/502; A61K 31/704; A61P 35/02; A61P 35/00; C12Q 1/6886; C12Q 2600/158; C12Q 2600/106; G01N 33/5748
USPC .......................................................... 514/34
See application file for complete search history.

(56) References Cited

U.S. PATENT DOCUMENTS

| | | |
|---|---|---|
| 2012/0134986 A1 | 5/2012 | Alizadeh et al. |
| 2016/0032398 A1 | 2/2016 | Pachynski et al. |

FOREIGN PATENT DOCUMENTS

| | | | |
|---|---|---|---|
| WO | WO-2014/138101 | | 9/2014 |
| WO | WO 2016/012630 | * | 1/2016 |

OTHER PUBLICATIONS

Alizadeh et al. Distinct types of diffuse large B-cell lymphoma identified by gene expression profiling. Nature vol. 403, p. 503-511 , Feb. 3, 2000. (Year: 2000).*
G Del Conte et al., "Phase I study of olaparib in combination with liposomal doxorubicin in patients with advanced solid tumours", British Journal of Cancer, vol. 111, No. 4, pp. 651-659 (Jul. 15, 2014).
American Type Culture Collection ATCC, HCC1187 BL ATCC CRL2323, pp. 1-2 (2015).
Andreassen et al., DNA damage responses and their many interactions with the replication fork, *Carcinogenesis*. 27:883-92 (2006).
Ashworth, A synthetic lethal therapeutic approach: poly(ADP) ribose polymerase inhibitors for the treatment of cancers deficient in DNA double-strand break repair, *J. Clin. Oncol*. 26:3785-90 (2008).
Audeh et al., Oral poly(ADP-ribose) polymerase inhibitor olaparib in patients with BRCA1 or BRCA2 mutations and recurrent ovarian cancer: a proof-of-concept trial, *Lancet*. 376:245-51 (2010).
Bryant et al., Specific killing of BRCA2-deficient tumours with inhibitors of poly(ADP-ribose) polymerase, *Nature*. 434:913-7 (2005).
Cancer Facts & Figures 2016, American Cancer Society.
Chambers et al., LMO2 at 25 years: a paradigm of chromosomal translocation proteins, *Open Biol*. 5:150062 (2015).
Coiffier et al., CHOP chemotherapy plus rituximab compared with CHOP alone in elderly patients with diffuse large-B-cell lymphoma, *N. Engl. J. Med*. 346:235-42 (2002).
Cubedo et al., Identification of LMO2 transcriptome and interactome in diffuse large B-cell lymphoma, *Blood*. 119:5478-91 (2012).
Drexler et al., Malignant hematopoietic cell lines: in vitro models for double-hit B-cell lymphomas, *Leuk. Lymphona*. 57:1015-20 (2016).
Dunleavy, Optimal Management of Double-Hit Lymphoma, *J. Oncol. Pract*. 12:241-2 (2016).
Duweb, Analysis of NEIL3 Expression: A Possible Resistance Factor to Cancer Chemotherapy in Paediatric Cancer Cells, pp. 16-17 (2015).
Farmer et al., Targeting the DNA repair defect in BRCA mutant cells as a therapeutic strategy, *Nature*. 434:917-21 (2005).
Fong et al., Inhibition of poly(ADP-ribose) polymerase in tumors from BRCA mutation carriers, *N. Engl. J. Med*. 36:123-34 (2009).
GenBank Accession No. AAH35607.1m LMO2 protein [*Homo sapiens*], Oct. 7, 2003.
GenBank Accession No. BC035607.1, *Homo sapiens* LIM domain only 2 (rhombotin-like 1), mRNA (cDNA clone MGC:45171 IMAGE:5186480), complete cds, Oct. 7, 2003.
Habermann et al., Rituximab-CHOP versus CHOP alone or with maintenance rituximab in older patients with diffuse large B-cell lymphoma, *J. Clin. Oncol*. 24:3121-7 (2006).
International Preliminary Reporton Patentability, PCT/US2017/058557 (dated Apr. 30, 2019).

(Continued)

*Primary Examiner* — Yih-Horng Shiao
(74) *Attorney, Agent, or Firm* — Marshall, Gerstein & Borun LLP

(57) ABSTRACT

The present disclosure relates, in general, a method of diagnosing and treatment of lymphoproliferative disorders.

22 Claims, 13 Drawing Sheets

Specification includes a Sequence Listing.

(56) References Cited

OTHER PUBLICATIONS

International Search Report and Written Opinion, PCT/US2017/058557 (dated Jan. 4, 2018).
Jackson et al., The DNA-damage response in human biology and disease, *Nature*. 461:1071-8 (2009).
Jaffe et al., Classification of lymphoid neoplasms: the microscope as a tool for disease discovery, *Blood*. 112:4384-99 (2008).
Mateo et al., DNA-Repair Defects and Olaparib in Metastatic Prostate Cancer, *N. Engl. J. Med*. 373:1697-708 (2015).
Matthews et al., LIM-domain-only proteins in cancer, *Nat. Rev. Cancer*. 13:111-22 (2013).
McDonnell et al., NPM-ALK signals through glycogen synthase kinase 3β to promote oncogenesis, *Oncogene*. 31:3733-40 (2012).
Nam et al., The role of LMO2 in development and in T cell leukemia after chromosomal translocation or retroviral insertion, *Mol. Ther*. 13:15-25 (2006).
Neale et al., Expression of the proto-oncogene rhombotin-2 is identical to the acute phase response protein metallothionein, suggesting multiple functions, *Cell Growth Differ*. 6:587-96 (1995).
Petrich et al., Impact of induction regimen and stem cell transplantation on outcomes in double-hit lymphoma: a multicenter retrospective analysis, *Blood*. 124:2354-61 (2014).
Pierce et al., Comparative antiproliferative effects of iniparib and olaparib on a panel of triple-negative and non-triple-negative breast cancer cell lines, *Cancer Biol. Ther*. 14:537-45 (2013).
Sambrook et al., Molecular Cloning: A Laboratory Manual, Cold Spring Harbor Laboratory, Cold Spring Harbor, NY (2001).
Shimo et al., Antitumor and anticancer stem cell activity of a poly ADP-rlbose polymerase inhibitor olaparib in breast cancer cells, *Breast Cancer*. 21:75-95 (2014).
Sonoda et al., Rad51-deficient vertebrate cells accumulate chromosomal breaks prior to cell death, *EMBO J*. 17:598-608 (1998).
Stordal et al., BRCA1/2 mutation analysis in 41 ovarian cell lines reveals only one functionally deleterious BRCA1 mutation, *Mol. Oncol*. 7:567-79 (2013).
Subramaniam et al., Lymphoma and other lymphoproliferative disorders in inflammatory bowel disease: a review, *J. Gastroenterol Hepatol*. 28:24-30 (2013).
Warren et al., The oncogenic cysteine-rich LIM domain protein rbtn2 is essential for erythroid development, *Cell*. 78:45-57 (1994).
Williamson et al., ATM deficiency sensitizes mantle cell lymphoma cells to poly(ADP-ribose) polymerase-1 inhibitors, *Mol. Cancer Ther*. 9:347-57 (2010).

\* cited by examiner

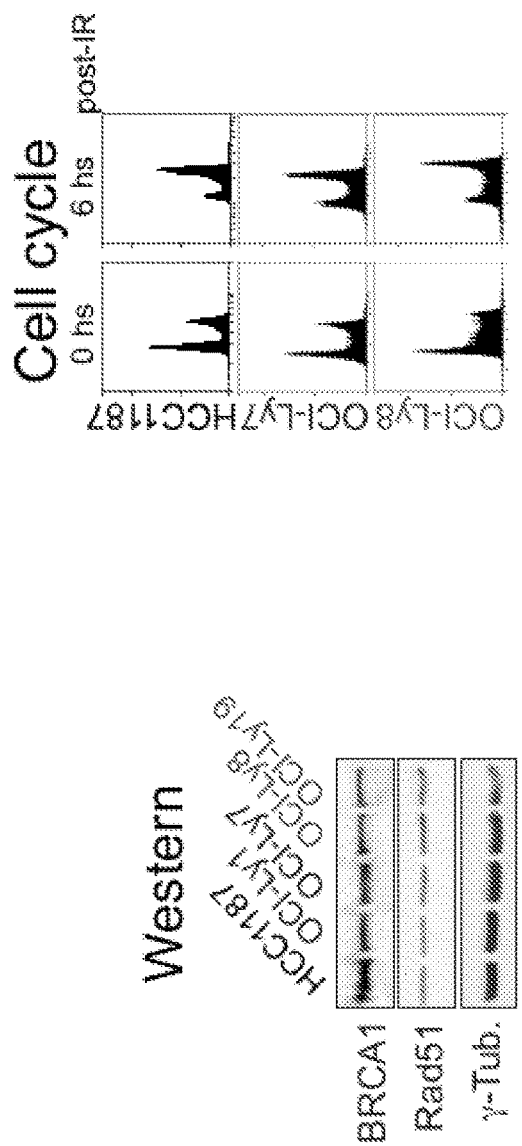
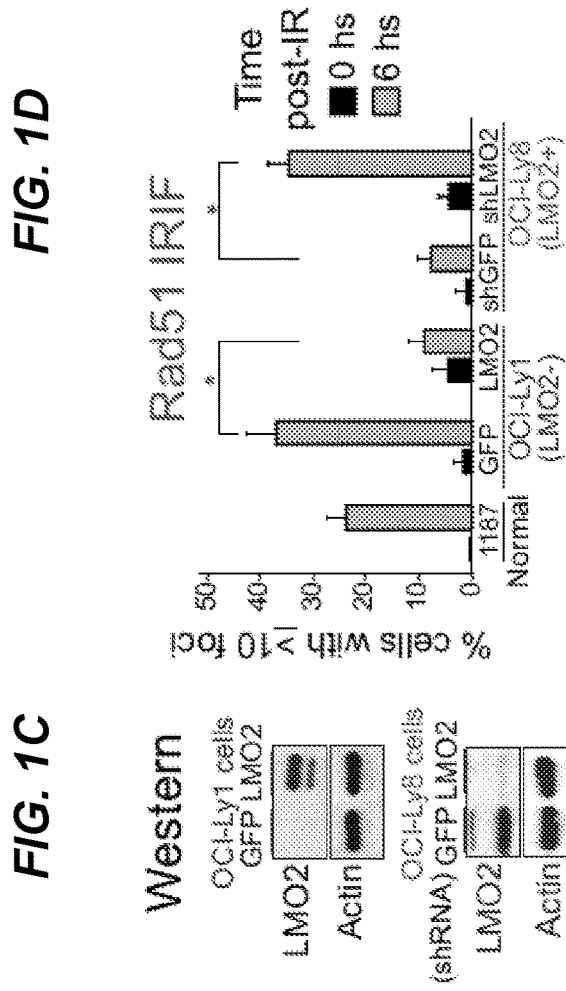

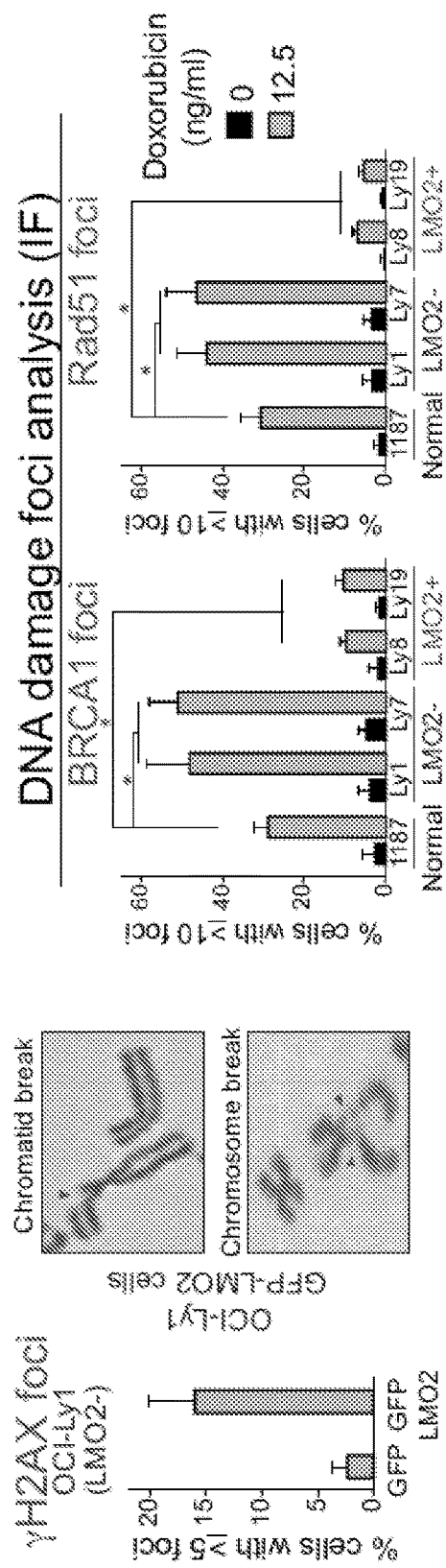
FIG. 1F
FIG. 1G
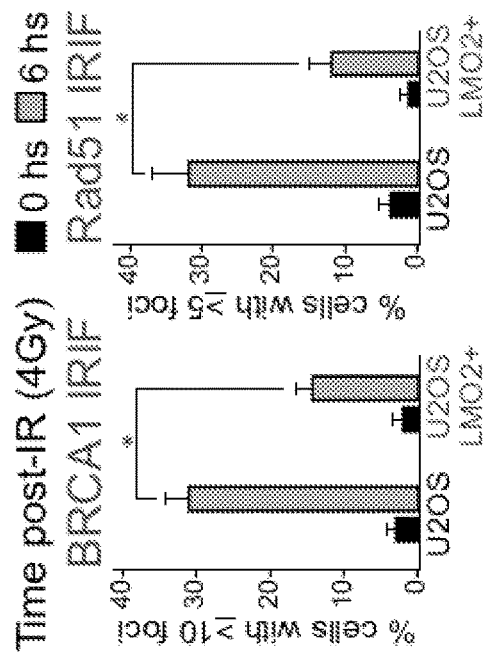
FIG. 1H

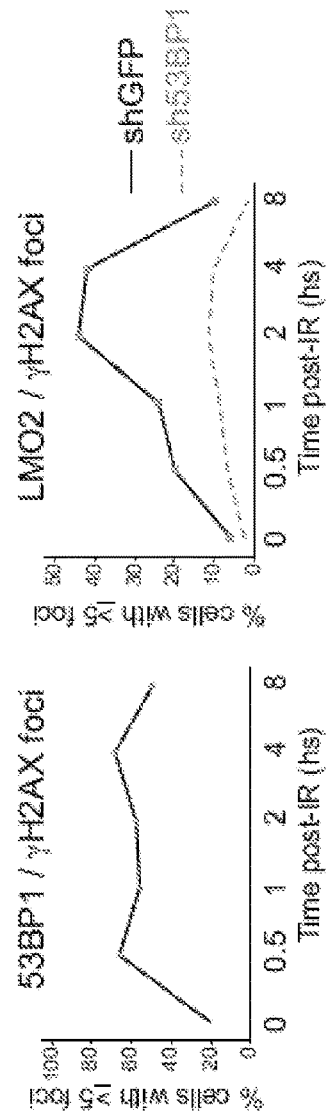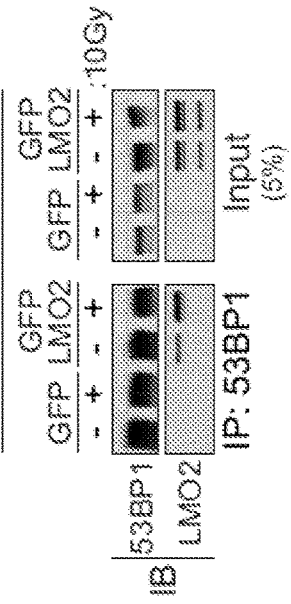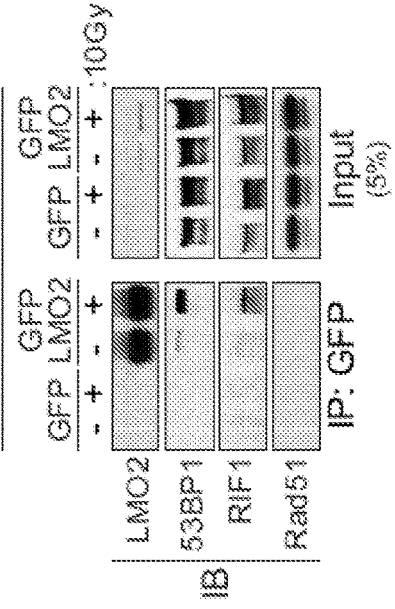
FIG. 2A
FIG. 2B

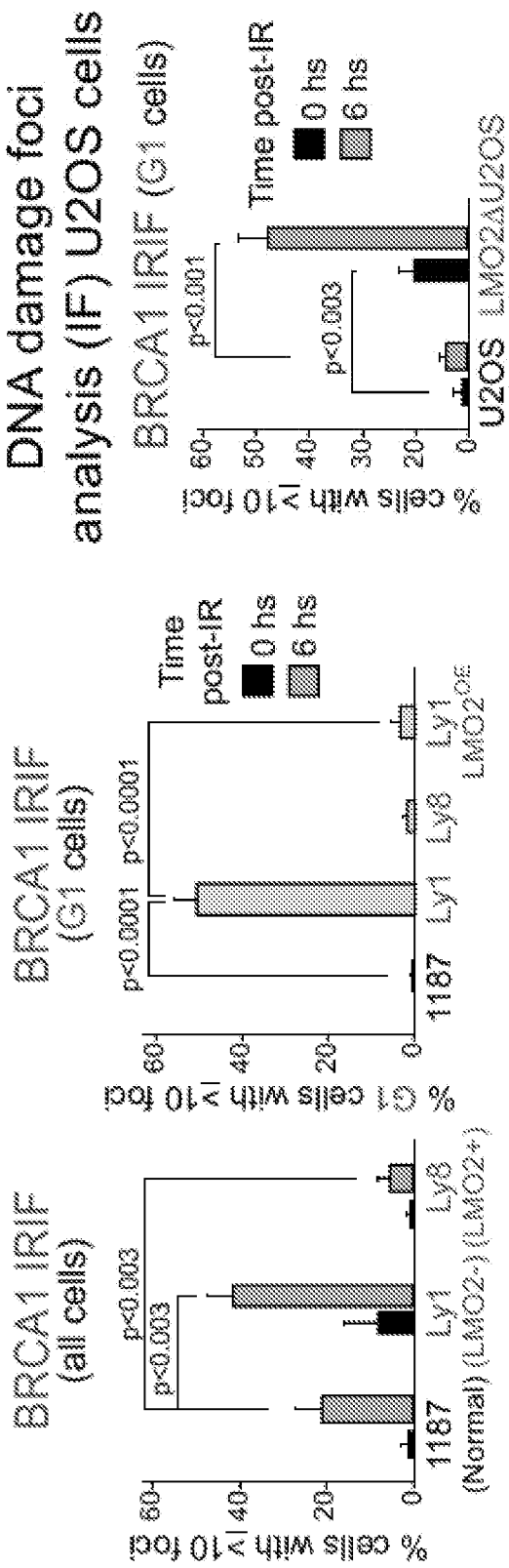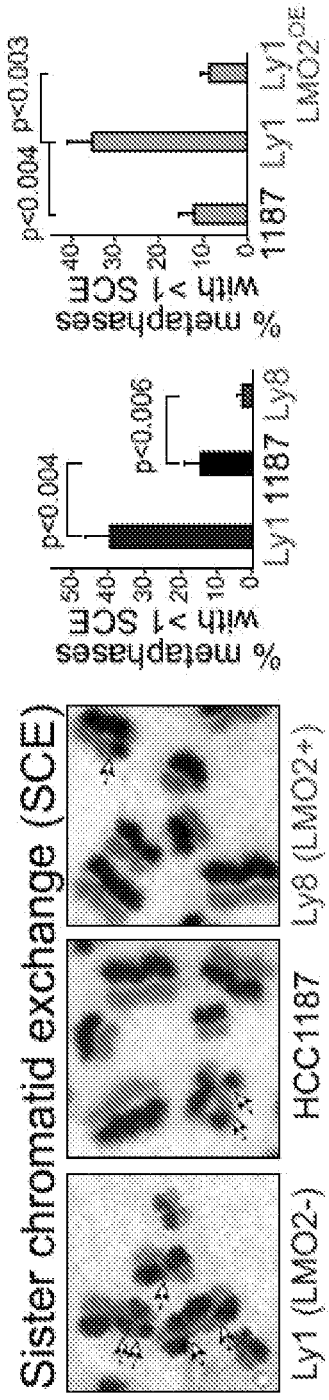
FIG. 3A
FIG. 3B
FIG. 3C

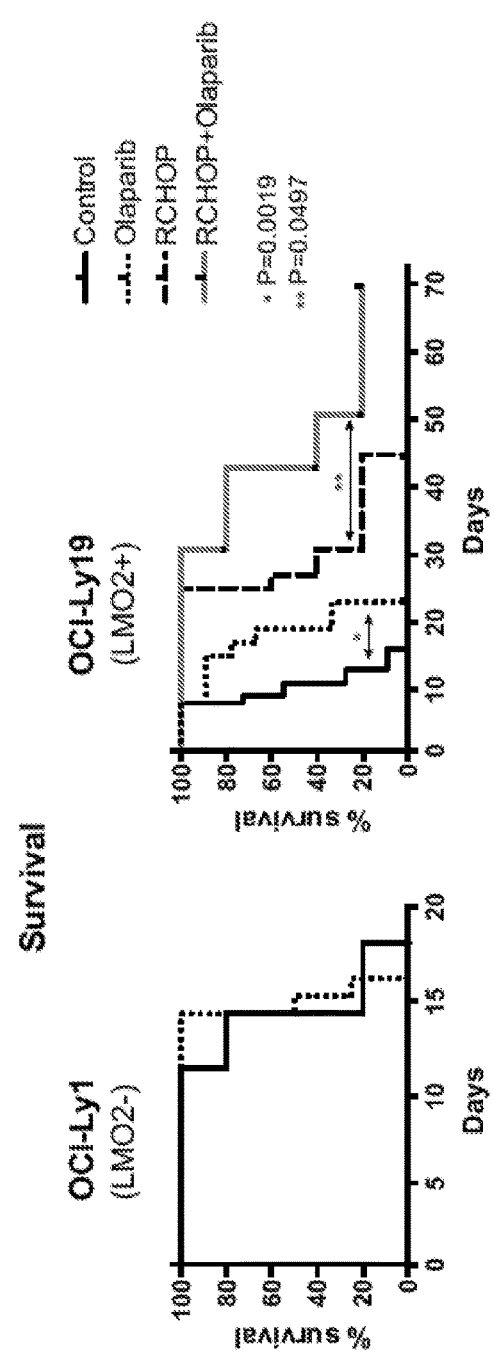
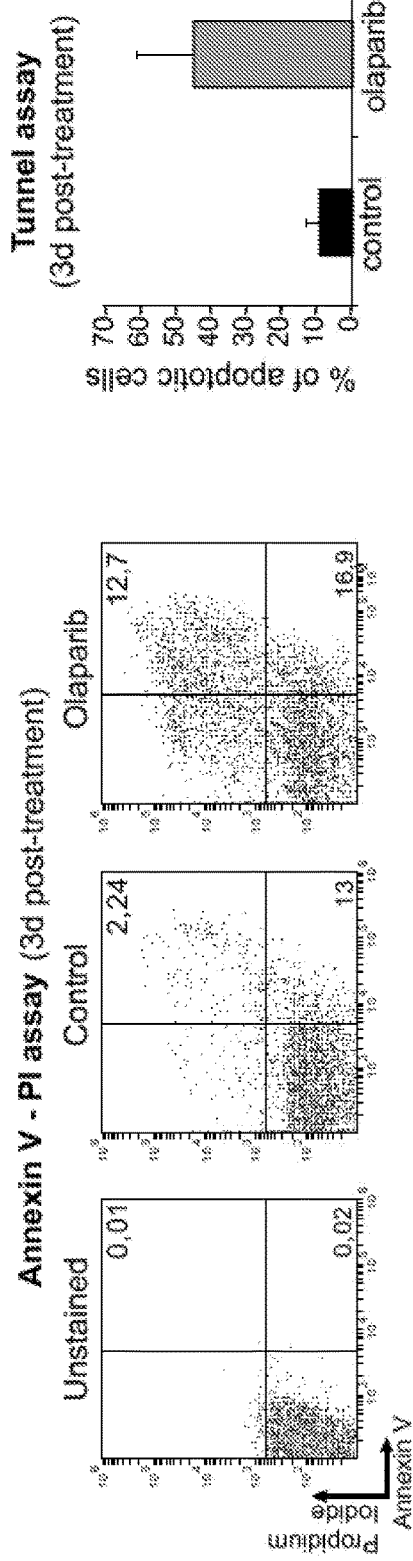
FIG. 5A
FIG. 5B
FIG. 5C

DIAGNOSIS AND TREATMENT OF LYMPHOPROLIFERATIVE DISORDERS WITH PARP INHIBITORS

CROSS-REFERENCE TO RELATED APPLICATIONS AND INCORPORATION BY REFERENCE OF MATERIAL SUBMITTED ELECTRONICALLY

This application is a national phase of PCT/US2017/058557, filed Oct. 26, 2017, which claims priority to U.S. Provisional Patent Application No. 62/413,812, filed Oct. 27, 2016, the disclosure of which is hereby incorporated by reference in its entirety.

Incorporated by reference in its entirety is a computer-readable nucleotide/amino acid sequence listing submitted concurrently herewith and identified as follows: Filename: 51252A_Seqlisting.txt; Size: 4,277 bytes; Created: Apr. 25, 2019.

FIELD OF THE INVENTION

The present disclosure relates, in general, a method of treating lymphoproliferative disorders using a Poly (ADP-ribose) polymerase (PARP) 1/2 inhibitor.

BACKGROUND

Lymphoproliferative disorders are a heterogeneous group of at least 70 conditions that result from the clonal proliferation of B-cells, T-cells, and natural killer (NK) cells. They are typically classified into four groups: 1) disorders of mature B cells (including chronic lymphocytic leukemia, follicular lymphoma, and diffuse large B-cell lymphoma (DLBCL)); 2) disorders of mature T and NK cells; 3) Hodgkin's lymphoma; and 4) post-transplantation lymphoproliferative disorders (PTLDs) (Jaffe et al., *Blood* 112: 4384-4399 (2008); Subramaniam et al., *J Gastroenterol Hepatol.* 28(1):24-30 (2013)).

Despite recent advances in treatment, cancers of the lymphatic system, or lymphomas, remain common. In the United States, more than 80,000 people are diagnosed with lymphoma each year, including more than 70,000 cases of non-Hodgkin's Lymphoma (NHL) (Cancer Facts & FIGS. 2016, American Cancer Society). Of NHLs, the most common type is DLBCL. In the case of DLBCL, ~50% of patients still succumb to DLBCL with current treatment methods (Habermann et al., *Journal of Clinical Oncology* 24, 3121-3127 (2006)), demanding discovery of novel molecular targets and therapeutic approaches to better diagnose and treat these lymphoproliferative disorders.

SUMMARY OF THE INVENTION

The disclosure provides a method of treating a lymphoproliferative disorder in a mammalian subject. The method comprises the following steps: a) measuring LIM domain only 2 (LMO2) in B-lymphocytes isolated from a mammalian subject suffering from a lymphoproliferative disorder and detecting an increase in the level of LMO2 compared to LMO2 levels in a mammal that is not suffering from a lymphoproliferative disorder; and b) administering an effective amount of Poly (ADP-ribose) polymerase (PARP) 1/2 inhibitor to the mammalian subject. In one aspect, the disclosure provides a method of treating acute lymphoblastic leukemia in a mammalian subject, the method comprising: a) measuring LMO2 in lymphocytes isolated from a mammalian subject suffering from acute lymphoblastic leukemia and detecting an increase in the level of LMO2 compared to LMO2 levels in a mammal that is not suffering from acute lymphoblastic leukemia; and b) administering an effective amount of PARP 1/2 inhibitor to the mammalian subject.

It is understood that each feature or embodiment, or combination, described herein is a non-limiting, illustrative example of any of the aspects of the invention and, as such, is meant to be combinable with any other feature or embodiment, or combination, described herein. For example, where features are described with language such as "one embodiment", "some embodiments", "further embodiment", "specific exemplary embodiments", and/or "another embodiment", each of these types of embodiments is a non-limiting example of a feature that is intended to be combined with any other feature, or combination of features, described herein without having to list every possible combination. Such features or combinations of features apply to any of the aspects of the invention. Where examples of values falling within ranges are disclosed, any of these examples are contemplated as possible endpoints of a range, any and all numeric values between such endpoints are contemplated, and any and all combinations of upper and lower endpoints are envisioned.

The headings herein are for the convenience of the reader and not intended to be limiting. Additional aspects, embodiments, and variations of the invention will be apparent from the Detailed Description and/or Drawing and/or claims.

BRIEF DESCRIPTION OF THE DRAWINGS

FIGS. 1A-1H: High levels of LMO2 protein inhibit BRCA1 and Rad51 foci after DNA damage. FIG. 1A, Western blots showing LMO2 level in the indicated cell lines. HCC1187 human lymphoblasts were used as control cells to determine normal level of LMO2 protein expression in lymphoid cells and T cell-derived Jurkat cells as negative control. Based on the LMO2 protein levels DLBCL cell lines were divided in LMO2− or LMO2+. FIG. 1B, quantification of γH2AX, 53BP1, BRCA1 and Rad51 ionizing radiation induced foci (IRIF) in the indicated cell lines. *, $p<0.002$ Student's t tests. FIG. 1C, Western blot for the indicated proteins in HCC1187 lymphoblasts and DLBCL cell lines. FIG. 1D, cell cycle analysis via propidium iodide staining before and 6 hs post-exposure to ionizing radiation (10Gy). FIG. 1E, left panel, Western blot showing LMO2 levels in OCI-Ly1 expressing GFP or LMO2 protein and OCI-Ly8 cells expressing shGFP or shLMO2. FIG. 1E, right panel, quantification of Rad51 and BRCA1 IRIF in the indicated cell lines. *, $p<0.001$ Student's t tests. FIG. 1F, left panel, quantification of γH2AX damage foci in OCI-Ly1 cells 2 days after introducing either GFP or a GFP-LMO2 fusion protein. FIG. 1F, right panel, micrographs showing chromatid or chromosome breaks in OCI-Ly1 cells expressing GFP-LMO2. FIG. 1G, quantification of BRCA1 and Rad51 damage foci in the indicated cell lines exposed during 24 hs to doxorubicin (12.5 ng/ml). *, $p<0.003$ Student's t test. FIG. 1H, quantification of Rad51 and BRCA1 IRIF in the indicated cells. *, $p<0.001$ Student's t test. Bars represent SD values obtained from three independent experiments. At least 50 cells were analyzed per cell line in each experiment.

FIGS. 2A-2C: LMO2 forms a complex with 53BP1 after DNA damage. FIG. 2A, Time course analyses of 53BP1 and LMO2 IRIF in the indicated cell lines post-IR (10Gy). In all cases γH2AX staining was used as IRIF marker. sh53BP1, shRNA against 53BP1. shGFP, shRNA against GFP. FIG.

2B, immunoblots (IB) of immunoprecipitation (IP) assays with nuclear extracts from OCI-Ly1 cells expressing or not a GFP-LMO2 fusion protein before and after (4 hs) exposure to IR (10Gy). FIG. 2C, quantification of BRCA1 and Rad51 IRIF in OCI-Ly8 cells expressing either shGFP or sh53BP1 6 hs after exposure to 10 Gy. P values from Student's t test. Bars represent SD values obtained from three independent experiments. At least 50 cells analyzed per cell line in each experiment.

FIGS. 3A-3C: LMO2 protein inhibits BRCA1 foci in G1 in multiple cell lines. FIG. 3A, quantification of BRCA1 foci in the indicated cell lines. Ly1-LMO2OE-OCI-Ly1 cells over-expressing LMO2 protein; 1187-HCC1187 lymphoblasts. FIG. 3B, quantification of BRCA1 IRIF in Cyclin A-negative (G1 phase) U2OS and LMO2-null U2OS (LMO2ΔU2OS) cells 6 hs post-IR (4Gy). FIG. 3C, DLBCL or HCC1187 cells grown for 32 hs in presence of BrdUTP were fixed and metaphases prepared to visualize individual sister chromatids. Sister chromatid exchanges (SCEs) in metaphase chromosomes are indicated with arrows in the images. The charts show the mean SCEs in metaphase spreads from the indicated cells. In all panels p-values from Student's t tests are shown. Bars represent SD values obtained from three independent experiments. At least 50 cells for IF or metaphases in SCE studies analyzed per cell line in each experiment.

FIG. 4A, MTS assay to evaluate effect of olaparib on the proliferation of human lymphoblasts (HCC1187), human primary lung fibroblasts (IMR90) and human lymphomas cells (LMO2 negative (U2932, OCI-Ly1) and LMO2 positive (DOHH2, OCI-Ly8, OCI-Ly19)). *P<0.0001. Two-way ANOVA. FIG. 4B, quantification of colony formation assays in OCI-Ly1, DOHH2, VaL and Val (LMO2 KO)-LMO2-null Val cells exposed to different concentrations of olaparib. Only colonies with 50 or more cells where counted. *P<0.001, Two-way ANOVA. FIG. 4C, quantification of the flow cytometer results for Propidium Iodide (PI) and Annexin V staining after 4 days in presence or absence of 1 μM olaparib for cell death analysis in the indicated lymphoma cell lines. FIG. 4D, representative pictures of colony formation assay quantified in FIG. 4B using DOHH2 cells. FIG. 4E, colony formation assay in DLBCL cells (LMO2 negative OCI-Ly1) and LMO2 positive cells (OCI-Ly8, OCI-Ly19, DOHH2)) exposed to different concentrations of olaparib alone or in combination with doxorubicin, etoposide, or carboplatin to reveal the synergism between PARP1 inhibition and genotoxic agents used in DLBCL treatment. CI, Combination Index (CI<1 indicates a synergistic effect). FIG. 4F, quantification of γH2AX DNA damage foci in OCI-Ly8 cells exposed to or not exposed to olaparib during 24 hs.

FIGS. 5A-5C: Olaparib slows growth of human DLBCL cells expressing LMO2 in vivo and prolongs survival in a murine xenograft model. Subcutaneous xenograft tumors were generated by human DLBCL cells (OCI-Ly19 or OCI-Ly1) injected into NOD/SCID (5 million cells/mouse). Treatment started when tumor reached 100 mm$^3$ (~10 days post-injection). FIG. 5A, Kaplan-Meier plots: OCI-Ly19 (n=per group: n=8 CTL, n=9 olaparib, n=5 RCHOP, n=5 RCHOP+olaparib) and OCI-Ly1 (n=5 per group). Mice were euthanized when the tumor volume reached 1500 mm$^3$ in accordance with the institutional guidelines. Statistical analysis was done by the log rank (Mantel-Cox) test. FIG. 5B, Ex vivo analyses of the tumors. The xenografts were generated as described above. Shown are representative FACS analyses of the OCI-Ly19 tumor cells exposed or not to olaparib during 3 days and stained with Annexin V and propidium iodide (PI). FIG. 5C, Tunnel assays in OCI-Ly19 tumor samples exposed or not to olaparib.

FIG. 6A, MTS assay to evaluate the effect of exposure to different concentrations of olaparib alone or in combination with doxorubicin in primary human DLBCL tumors expressing or not LMO2 and a Reactive follicular hyperplasia (LMO2–). CI, Combination Index (CI<1 indicates a synergistic effect). FIG. 6B, Western blots showing LMO2 level in human DLBCL cell lines (OCI-Ly1 (LMO2 negative), OCI-Ly19 (LMO2 positive), human primary lymphoblasts (HCC1187)), and primary human tumors (LMO2+, DLBCL expressing LMO2, LMO2–, DLBCL not expressing LMO2) and RFH-Reactive follicular hyperplasia not expressing LMO2. GAPDH was used as loading control. FIG. 6C, immunohistochemistry (IHC) for LMO2 in primary human DLBCL samples used for FIGS. 6A and 6B. H&E, hematoxylin and eosin staining.

FIG. 7A, quantification of cell proliferation via MTS assay in MOLT16 (LMO2+) and Jurkat (LMO2–) T cell lymphoblastic leukemia cell lines exposed to different concentrations of olaparib during 4 days. *P<0.001, Two-way ANOVA. FIG. 7B, quantification of the flow cytometer results for Annexin V staining after 4 days in presence or absence of indicated concentrations of olaparib for cell death analysis in the indicated T cell lymphoblastic leukemia cell lines.

DETAILED DESCRIPTION

Figure 1A:
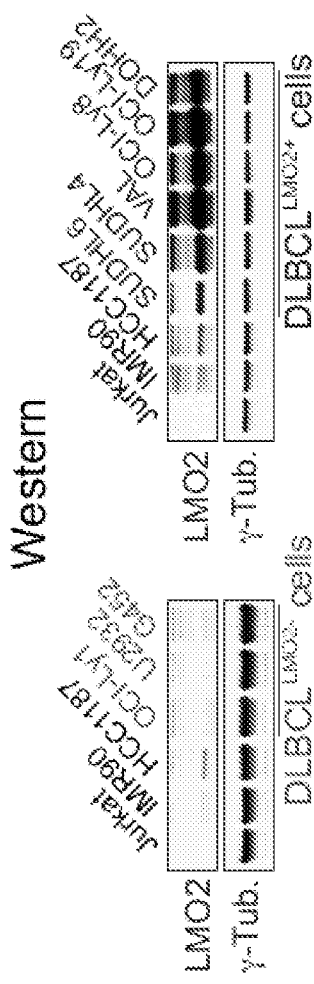

The invention provides a method of treating lymphoproliferative disorders by measuring LMO2 in B-lymphocytes isolated from a mammalian subject suffering from a lymphoproliferative disorder and detecting an increase in the level of LMO2 and administering an effective amount of PARP 1/2 inhibitor to the mammalian subject. The invention provides a significant advancement by allowing identification a lymphoproliferative disorder patient population that possesses homologous recombination (HR) defective DNA repair and can be treated with a PARP1/2 inhibitor.

The terminology used herein is for the purpose of describing particular embodiments only and is not intended to be limiting.

"ABC" as used herein, refers to Activated B cell.

"BRCA1" as used herein refers to breast cancer gene 1.

"BRCA2" as used herein refers to breast cancer gene 2.

"BRCA1/2" as used herein refers to breast cancer genes 1 and 2.

"DLBCL" as used herein, refers to Diffuse Large B cell Lymphomas.

"DSBs" as used herein, refers to DNA double strand breaks.

"HR" as used herein, refers to homologous recombination.

"HCC1187" as used herein, refers to human Epstein Barr-Virus (EBV)-immortalized lymphoblast cell line.

"LMO2" as used herein, refers to LIM domain Only 2 gene.

A "mammalian subject" can be any mammal, such as a human. Contemplated mammalian subjects include, but are not limited to, animals of agricultural importance, such as bovine, equine, and porcine animals; animals serving as domestic pets, including canines and felines; animals typically used in research, including rodents and primates; large endangered species; and zoo animals such as primates, felines, giraffes, elephants, rhinos.

"Newly diagnosed lymphoproliferative disorder" as used herein, refers to a mammalian subject suffering from a lymphoproliferative disorder that has not been diagnosed with a lymphoproliferative disorder previously.

"NHEJ" as used herein, refers to non-homologous end-joining.

"Relapsed lymphoproliferative disorder" as used herein, refers to a mammalian subject that has been previously treated for a lymphoproliferative disorder and wherein the lymphoproliferative disorder has reemerged after a period of improvement.

"PARP1/2 inhibitors" or "PARPi" as used herein, refers to Poly(ADP-ribose) polymerase 1 and 2 inhibitors. PARP is an enzyme located in the nuclei of cells of various organs. PARP participates in a variety of DNA-related functions including cell proliferation, differentiation, apoptosis, and DNA repair. Examples of PARPi include, but are not limited to, It olaparib, veliparib, iniparib, rucaparib, niraparib, talazoparib, CEP-9722, and INO-1001.

The term "lymphoproliferative disorder" as used herein, refers to a condition wherein lymphocyte growth/division is uncontrolled. Excessive lymphocyte growth leads to tumor, which may be malignant or benign. The terms "lymphoma" and "lymphoid malignancy" refer specifically to malignant tumors derived from lymphocytes and lymphoblasts. Examples of lymphoproliferative disorders include, but are not limited to, diffuse large B cell lymphoma (DLBCL), germinal center B cell-like diffuse large B cell lymphoma (GCB), activated B cell-like diffuse large B cell lymphoma (ABC), primary mediastinal B cell lymphoma (PMBL), double-hit lymphoma (DHL), follicular lymphoma (FL), Burkitt lymphoma (BL), mantle cell lymphoma (MCL), small cell lymphocytic lymphoma (SLL), mucosa-associated lymphoid tissue lymphoma (MALT), splenic marginal zone lymphoma (SMZL), nodal marginal zone lymphoma (NMZ), lymphoplasmacytic lymphoma (LPL), post-transplant lymphoproliferative disorder (PTLD), lymphoblastic lymphoma (LBL), B and T-cell acute lymphoblastic leukemia (B-ALL and T-ALL), double hit diffuse large B cell lymphoma, or multiple myeloma.

The LIM domain Only 2 (LMO2) gene is expressed in all tissues except mature T cells (Neale et al., *Cell Growth Differ* 6, 587-596 (1995)) and plays important roles in normal endothelial and hematopoietic cell development (Chambers and Rabbitts, *Open Biol.* 5, 150062 (2015); Matthews, *Nat Rev Cancer* 13, 111-122 (2013); Nam and Rabbitts. *Mol Ther* 13, 15-25, (2006); Warren et al., *Cell* 78, 45-57 (1994)). The amino acid sequence of human LMO2 is set forth in SEQ ID NO: 1 (NCBI GenBank: AAH35607.1), and the nucleic acid sequence of human LMO2 is set forth in SEQ ID NO: 2 (NCBI GenBank: BC035607.1).

The below described embodiments illustrate representative examples of methods of the disclosure. From the description of these embodiments, other aspects of the invention can be made and/or practiced based on the description provided below. The methods involve use of immunological and molecular biological techniques described in methodology treatises such as Current Protocols in Immunology, Coligan et al., ed., John Wiley & Sons, New York. Techniques of molecular biology are described in detail in treatises such as Molecular Cloning: A Laboratory Manual, 2nd ed., vol. 1-3, Sambrook et al., ed., Cold Spring Harbor Laboratory Press, Cold Spring Harbor, N.Y., 2001; and Current Protocols in Molecular Biology, Ausubel et al., ed., Greene Publishing and Wiley-Interscience, New York. General methods of medical treatment are described in McPhee and Papadakis, Current Medical Diagnosis and Treatment 2010, 49th Edition, McGraw-Hill Medical, 2010; and Fauci et al., Harrison's Principles of Internal Medicine, 17$^{th}$ Edition, McGraw-Hill Professional, 2008.

The disclosure provides a method of treating a lymphoproliferative disorder. The method comprises a) measuring LMO2 in B-lymphocytes isolated from a mammalian subject suffering from a lymphoproliferative disorder and detecting an increase in the level of LMO2 compared to LMO2 levels in a mammal that is not suffering from a lymphoproliferative disorder; and b) administering an effective amount of PARP1/2 inhibitor to the mammalian subject. In various embodiments, mammalian subject is a human subject and the lymphoproliferative disorder is lymphoma. In various embodiments, the lymphoproliferative disorder is acute lymphoblastic leukemia (ALL).

The method comprises detecting an increase in LMO2 levels in the subject compared to LMO2 levels in a mammal that is not suffering from the lymphoproliferative disorder. In this regard, LMO2 is optionally detected in 30% or more of malignant B-lymphocytes present in a tumor biopsy from the mammalian subject. Non-affected mammals typically do not have a B-lymphocyte subpopulation comprising 30% or more of the total population and which produce LMO2. Alternatively or in addition, the LMO2 level in B-lymphocytes from the mammalian subject is higher than the level of LMO2 observed in human Epstein Barr-Virus (EBV)-immortalized lymphoblast cell line (HCC1187, ATCC). The HCC1187 cell line serves as a surrogate for the level of LMO2 from a non-affected mammalian organ.

In various embodiments, the disclosure provides a method of treating acute lymphoblastic leukemia (ALL). The method comprises a) measuring LMO2 in lymphocytes isolated from a mammalian subject suffering from ALL and detecting an increase in the level of LMO2 compared to LMO2 levels in a mammal that is not suffering from ALL; and b) administering an effective amount of PARP 1/2 inhibitor to the mammalian subject. In various embodiments, the acute lymphoblastic leukemia is B-cell ALL or T-cell ALL. The method comprises detecting an increase in LMO2 levels in the subject compared to LMO2 levels in a mammal that is not suffering from the ALL. In this regard, LMO2 is optionally detected in 30% or more of malignant B-lymphocytes or T-lymphocytes present in a tumor biopsy from the mammalian subject. Non-affected mammals typically do not have a B-lymphocyte subpopulation comprising 30% or more of the total population and which produce LMO2. Alternatively or in addition, the LMO2 level in B-lymphocytes or T-lymphocytes from the mammalian subject is higher than the level of LMO2 observed in human Epstein Barr-Virus (EBV)-immortalized lymphoblast cell line (HCC1187, ATCC). The HCC1187 cell line serves as a surrogate for the level of LMO2 from a non-affected mammalian organ.

LMO2 levels are measured using any suitable assay. For example, in various embodiments, RNA levels are measured. In this regard, LMO2 RNA levels are optionally measured via real time polymerase chain reaction (qRT-PCR) or RNA-Sequencing. Alternatively or in addition, LMO2 protein levels are measured. LMO2 protein levels are optionally measured by immunohistochemistry (IHC), flow cytometry or Western blotting.

The method further comprises administering a PARP1/2 inhibitor to the subject. In various embodiments, the PARP 1/2 inhibitor is olaparib, veliparib, iniparib, rucaparib, niraparib, talazoparib, CEP-9722, or INO-1001. In exemplary embodiments, the PARP 1/2 inhibitor is olaparib.

In various aspects of the disclosure, a PARP1/2 inhibitor is administered in an amount and for a time sufficient to reduce tumor volume or tumor burden in the mammalian subject. Without wishing to be bound to a particular theory, it is believed that PARP1/2 inhibitors induce cell death in HR-deficient, tumor cells with high levels of LMO2. The method herein reduces tumor volume or tumor burden in the subject, and/or reduces metastasis in the mammalian subject. Tumor volume can be measured using methods such as, for example, computed tomographic (CT) scan or positron emission tomography (PET) imaging. Tumor burden can be determined by, e.g., measuring tumor markers in biological samples. In various embodiments, the method reduces tumor volume or tumor burden by at least 1%, 3%, 5%, 10%, 20%, 30% or more. In various embodiments, the method reduces tumor volume or tumor burden by at least 10%, 15%, 20%, 25%, 30%, 35%, 40%, 45%, 50%, 55%, 60%, 65%, 70%, 75%, 80%, 85%, 90%, 95% or 100%. Ranges containing any of the aforementioned integers as lower and upper ends are contemplated (e.g., 10%-50% or 3%-50%). It will be appreciated that complete eradication of the tumor or tumor burden is not required to achieve a beneficial response; any level of reduction of tumor burden, tumor volume, or metastasis is contemplated.

Suitable methods of administering a physiologically-acceptable composition, such as a sterile pharmaceutical composition comprising a PARP1/2 inhibitor, are well known in the art. For example, a PARP1/2 inhibitor, olaparib, can be administered orally or intravenously (Center for drug evaluation and research, Application no.: 206162Orig1s000, LYNPARZA (olaparib) (www.accessdatalda.gov/drugsatfda_docs/nda/2014/206162Orig1s000PharmR.pdf).

In various aspects, a PARP1/2 inhibitor is administered in an amount sufficient to reduce the symptoms of a lymphoproliferative disorder described herein. In general, doses of PARP 1/2 inhibitor employed for mammalian subject treatment are in the range of about 1 mg/kg to about 1000 mg/kg per day. In related embodiments, the dose of PARP1/2 inhibitor is between 1-10 mg/kg, 1-100 mg/kg, 100-200 mg/kg, 200-400 mg/kg, 400-800 mg/kg, 800-1000 mg/kg. The desired dose may be conveniently administered in a single dose, or as multiple doses administered at appropriate intervals, for example, as two, three, four or more sub-doses per day.

In various embodiments, the mammalian subject has a relapsed lymphoproliferative disorder and is treated with a PARP 1/2 inhibitor alone. In other embodiments, the mammalian subject has a newly diagnosed lymphoproliferative disorder.

In various aspects, the method further comprises administering a second chemotherapeutic agent or combination of agents, such as agents useful in treating a lymphoproliferative disorder. The PARP1/2 inhibitor and chemotherapeutic agent(s) may be given simultaneously, in the same formulation, or administered in separate formulations and administered concurrently (e.g. agents given within 30 minutes of each other). Concurrent administration of two therapeutic agents does not require that the agents be administered at the same time or by the same route, as long as there is an overlap in the time period during which the agents are exerting their therapeutic effect. Simultaneous or sequential administration is contemplated, as is administration on different days or weeks.

Chemotherapeutic agents contemplated for use with the PARP1/2 inhibitors include, but are not limited to, doxorubicin, cisplatin, bleomycin, vinblastine, dacarbazine, bleomycin, etoposide, cyclophosphamide, vincristine, procarbazine, prednisolone, carmustine, etoposide, cytarabine, melphalan, CHOP, COPP, CVP, EPOCH, Hyper-CVAD, ICE, R-CHOP, R-CVP, R-EPOCH, and/or R-ICE, R-DHAP, McGrath protocol or myeloablative regimens or these regimens with other antibodies directed to CD20 or other surface proteins expressed by B cell tumors.

It is further contemplated that other adjunct therapies may be administered, where appropriate. For example, the subject may also be administered additional cytotoxic agents, photodynamic therapy and/or radiation therapy, or have undergone a surgical procedure (e.g. tumor resection). Additional aspects and details of the disclosure will be apparent from the following examples, which are intended to be illustrative rather than limiting.

EXAMPLES

Materials and Methods

Primary antibodies were used in this study: mouse anti-γH2AX (Millipore), rabbit anti-γH2AX (Cell Signaling Technology) mouse anti-53BP1 (Novus Biological), rabbit anti-53BP1 (Millipore), rabbit anti-Rad51 (Santa Cruz), mouse anti-BRCA1 (D-9, Santa Cruz), mouse anti-conjugated Ubiquitin (FK2 clone, Millipore), GAPDH, rabbit anti-Rap80 (Bethyl Labs), rabbit anti-RIF1 (Bethyl Labs), rabbit anti-Cyclin A (Santa Cruz). Rabbit Anti-RNF168 (Millipore), mouse anti-RAP1 (Santra Cruz), Mouse monoclonal anti-LMO2 antibody was generated in our laboratory. Secondary antibodies: 488 Fluor Goat secondary antibody (Invitrogen), 568 Fluor Goat secondary antibody (Invitrogen), 647 Fluor Goat secondary antibody (Invitrogen).

Diffuse Large B-cell lymphoma cell lines: Human cell lines OCI-LY1, OCI-LY7, OCI-LY8, U2932, DOHH2, OCI-LY19, SUDHL-6 were cultured with IMDM Iscove Modified Dulbecco medium (Gibco BRL) supplemented with 20% human plasma, 2 mM glutamine (Gibco BRL), and 100 U/L penicillin/streptomycin (Gibco BRL).

Primary tumors were obtained from DLBCL or no DLBCL patients following appropriate consent of the IRB approved protocol and single cell suspension generated using standard techniques.

Lymphoblast HCC1187 cell was cultured with IMDM Iscove Modified Dulbecco medium (Gibco BRL) supplemented with 20% human plasma, 2 μM glutamine (Gibco BRL), and 100 U/L penicillin/streptomycin (Gibco BRL) and 2 μM non-essential amino acids.

Non-lymphoma cell lines: Hybridoma cells, human embryonic kidney 293TX cells and osteosarcoma U2OS cells were cultured in RPMI 1640 medium (Gibco BRL) supplemented with 10% FBS, 2 mM glutamine, and 100 U/L penicillin/streptomycin.

For overexpression of LMO2, doxycycline-inducible lentiviral vector containing green fluorescent protein (GFP) and FLAG double-tagged LMO2 vector construct was used.

For knockdown studies, human shLMO2 construct (TRCN0000017132) and 53BP1 shRNA constructs (TRCN0000018866); shGFP targeting human coding region (5'-GCAAGCTGACCCTGAAGTTCAT-3') were used. For Virus packaging: pCMV dR8.2 V pdeltaR and vesicular stomatitis Virus-G envelope plasmid (pCMV-VSV-G) were used. For knockdown studies, cells stably expressing short hairpin RNA were obtained by lentiviral delivery. HEK293T cells cotransfected with shRNAs together with the packaging vectors pCMV-dR8.2 dvpr and pCMV-VSV-G (3:1:1 ratio) using JetPrime transfection reagent (Polyplus). Seventy-two hours post-transfection, the cell medium containing the viral particles was collected and concentrated using Lenti-X concentrator (Clontech). Lymphoma cells were transduced with the concentrated lentivirus in media containing Protamine sulfate (2 µg/ml) (Sigma Aldrich). Forty-eight hours post-infection puromycin (2 µg/ml final) was added to start selection.

For generating LMO2 overexpressing cells, doxycycline-inducible lentiviral vector containing green fluorescent protein (GFP) and FLAG tags at the amino-terminal of full length LMO2 was used. Virus production and infection was done as described above. To select infected cells, doxycycline (0.5 µg/ml from sigma) added to the cells for two consecutive days, GFP positive cells were sorted as LMO2 overexpressing cells by flow cytometer (BD FACS Aria-IA sorter).

Whole cell extract preparation and western blot analysis: Whole cell extracts were prepared by lysing cells using RIPA buffer (1×PBS, 1% Nonidet P-40, 0.5% sodium deoxycholate, 0.1% SDS) plus proteinases inhibitors (10 mM phenylmethylsulfonyl fluoride, 1 µg/ml aprotinin, 100 mM sodium orthovanadate) on ice for 30 minutes. Protein concentration was determined with Coomassie Protein Assay Reagent (Pierce, Rockford Ill.). For western blotting, 30 µg of whole cell lysates per condition were separated on 10% SDS-polyacrylamide gels, transferred to nitrocellulose membranes (Bio-Rad Laboratories Inc., Hercules, Calif.), and placed in a transfer chamber for 1 h at 100V. After transfer, the nitrocellulose membrane was incubated in blocking solution (5% milk or 1% BSA in PBS) for 1 h at room temperature and immunoblotted with specific antibody diluted in blocking solution overnight at 4° C. Next, the membranes were washed in PBST (phosphate buffer saline with 1% tween-20) 4 times for 5 min each wash. Secondary antibodies conjugated to horseradish peroxidase (HRP) and Supersignal West Pico/femto chemiluminescent substrate (Thermo Scientific) were used to enable detection of protein by exposure to light-sensitive film and developing.

Immunoprecipitation: Cell lysate was prepared by mixing the cell pellet with lysis buffer (1% NP40 buffer with 10 mM phenylmethylsulfonyl fluoride) and incubated for 30 min on ice. The cell lysate was pre-cleaned with protein A or G slurry beads for 30 min at 4° C. 1-10 µg of antibody or IgG control added to the pre-cleaned cell lysate for overnight at 4° C. 50 µL, of Protein A or G slurry was added and incubated for 1 h at 4° C., and centrifuged at 2,500×g for 30 seconds at 4° C. The supernatant was removed completely and the beads washed 4 times with 500 µL, of ice-cold Lysis Buffer. After the last wash, the supernatant was aspirated carefully and 50 µL, of 1×SDS-PAGE sample loading buffer was added to the bead pellet, Western blot analysis was performed as described above.

Sister chromatid exchange: Lymphoma cells were grown in the presence of BrdU (10 µg/ml) for 32 hs. Four hours before collection of the samples, colcemid (20 ng/ml) was added to enrich the culture in mitotic cells. After colcemid incubation, cells were washed once with 1×PBS. The pellet resuspended in 10 mL of hypotonic solution (75 mM KCl) and incubated for 5 min. Next, cells were fixed with methanol/glacial acetic acid (3:1 v/v). The fixed cells were dropped onto a prechilled glass slide for suitable metaphase spread. After drying the samples overnight, the cells were stained with Hoechst 33528 (200 µg/ml) for 30 minutes after, which the slides were washed with water and air-dried again. Around 30 µl of McIlvaines buffer were added on the slide and covered with a 22×60 mm coverslip. The slides were irradiated with UV light for 30 min. Coverslips were removed carefully and rinsed with water and air-dried. The slides were then stained in Giemsa for about 10 min, fixed with xylene for 1 min, air-dried, and mounted with Permount. Chromosomes were observed with a light microscope under normal illumination.

Proliferation and cell cycle studies: Cell proliferation was studied using cell titer 96 Aqueous Non-radioactive cell proliferation (MTS) kit from Promega. This assay was performed following manufacturer's instructions. For cell cycle studies, cells were fixed with 70% cold ethanol and incubated overnight at 4° C. Next, cells were washed once with 1×PBS and incubated with 50 µg/ml Propidium Iodide (Invitrogen) and RNAse (0.1 mg/ml) for 30 min. Cells were analyzed using a flow cytometer (BD FACS Canto-II analyzer).

Immunofluorescence studies: For studying DNA break repair, DNA double-strand breaks were induced either by exposing the cells to ionization radiation (IR). DLBCL cell lines were exposed to gamma ray source at 10 Gy (cobalt 60 irradiator) and U2OS cells were exposed to 4 Gy. Alternatively double-stranded breaks were induced by adding Doxorubicin (12.5 ng/ml) to the culture during 16-20 hs. Cells were attached on a glass slide pre-coated with poly-lysine for 30 min. Cells were fixed with 4% Para-formaldehyde in 1×PBS for 15 min at room temperature. After fixing, cells were permeabilized using blocking solution (1 mg/ml BSA, 5% Goat/Horse normal serum, 0.5% TritonX-100) for 30 min. Cells were incubated with primary antibodies diluted in blocking solution for 1 h. Cells were washed three times with 1×PBS 5 min each. After washing, cells were incubated with secondary antibodies diluted in blocking solution, Alexa Fluor 488 or Alexa Fluor 594 for 30 min. Cells were then washed with 1×PBS twice for 5 min each wash. Nuclear DNA was visualized via DAPI (1 µg/ml) (Sigma Aldrich) staining for 15 min. Finally, cells were washed with 1×PBS for 15 min to remove excess stain and mounted with Prolong Gold antifade reagent (Invitrogen). Images were acquired using a Leica DMI6000 B Fluorescence microscope.

Colony-forming assay: Clonogenic assays were performed as described elsewhere (McDonnell, *Oncogene*, 31(32), 3733-3740 (2012)). In total, 500 cells were pre-treated with indicated olaparib concentration (0; 1; 10; 100; 1,000; and 10,000 nM) for 48 h and seeded in triplicate in MethoCult conditioned media (Stem Cell Technologies, Vancouver, Canada). After 14 days, macroscopic colonies were stained with iodonitrotetrazolium chloride (Sigma Aldrich) overnight and counted. Only colonies with 50 or more cells were counted.

All mice studies were conducted after approval of IACUC protocol. For DLBCL xenograft model, five-week-old female NOD/SCID mice (Harlan's) were subcutaneously injected with DLBCL cell line OCI-LY19 ($5×10^6$ cells/mouse) into the right flank. Once tumors reached 100 mm³, mice were subdivided into two experimental groups (n=5-7/group). One group received buffer solution (1×PBS) and the other group received Olaparib (50 mg/kg; LC Labs, MA) for 21 consecutive days via IP injection. In separate experiments, one group received buffer solution (1×PBS), second group received Olaparib (50 mg/kg; LC Labs, MA), third group RCHOP (Rituximab 20 mg/kg, i.v. for a single dose on D1; cyclophosphamide, 40 mg/kg, D1; doxorubicin, 3.3 mg/kg, i.v. D1; vincristine, 0.5 mg/kg, i.v. D1; and prednisone, 0.2 mg/kg, every day by oral gavage on D1-5 and fourth group combination of Olaparib with RCHOP. Tumor bearing mice were observed every two days for tumor volume and weight loss was measured using standard calipers. Once the tumor volume exceeded 1500 mm$^3$ or the mouse volume dropped more than 10% total body weight, the mice were sacrificed.

Example 1: DLBCL LMO2+ Cells have a HR-Dysfunction

LMO2 over-expression in DLBCL cells results in genetic instability, suggesting that high levels of LMO2 protein may compromise DNA repair (Cubedo et al., Blood 119, 5478-5491 (2012)). The data described herein demonstrate that LMO2 regulates DSB repair pathway choice. LMO2 was found to inhibit HR in the G1 phase, thereby restricting HR activity to the S/G2 phases. Consequently, DLBCL cells not expressing LMO2 (DLBCL$^{LMO2-}$) can use HR in the G1 phase to repair DSBs. Further, it was observed that a high concentration of LMO2, as found in DLBCL$^{LMO2+}$ cells, also inhibits HR in the S/G2 phases. These studies revealed that DLBCL LMO2+ cells have a HR-dysfunction that can be exploited to limit their proliferation and survival. This defect in DLBCL$^{LMO2+}$ cells is similar to the HR-dysfunction described in breast and ovarian cancers due to BRCA1/2 deficiency (Farmer et al., Nature 434, 917-921 (2005); Ashworth, A. Journal of clinical oncology 26, 3785-3790 (2008); Fong et al., NEJM 361, 123-134 (2009); Audeh et al., Lancet 376, 245-251 (2010)), which serves as predictive biomarker for response to Poly(ADP-ribose) polymerase 1 and 2 inhibitors (PARPi). BRCA1/2 mutant cells accumulate DNA breaks when exposed to PARPi, resulting in cell death. This "synthetic lethality" led to the FDA approval of the PARPi olaparib for treatment of BRCA1/2-defective ovarian cancer and castration resistant prostate cancer (Audeh et al., Lancet 376, 245-251 (2010); Mateo, J. et al. NEJM 373, 1697-1708 (2015)). Preliminary in vitro studies disclosed herein show that DLBCL$^{LMO2+}$ cells exhibit a high sensitivity to PARPi as manifested by decreased cell colony formation and proliferation due to cell death via apoptosis (Table 1). Further, PARP1/2 inhibition was found to synergize with chemotherapy employed in DLBCL patients. These findings identify a novel function for LMO2 and allow for the selection of lymphoproliferative disorder subjects that will respond to PARPi.

TABLE 1

High expression of LMO2 makes DLBCL cells sensitive to PARPi

|  | LMO2 protein level | | |
|---|---|---|---|
|  | Low | Normal | High |
| HR (G1) | + | − | − |
| HR (S/G2) | + | + | − |
| PARPi sens | − | − | + |

Example 2: LMO2 Inhibits BRCA1 and Rad51 Presence at DSB Sites

Figure 1B:
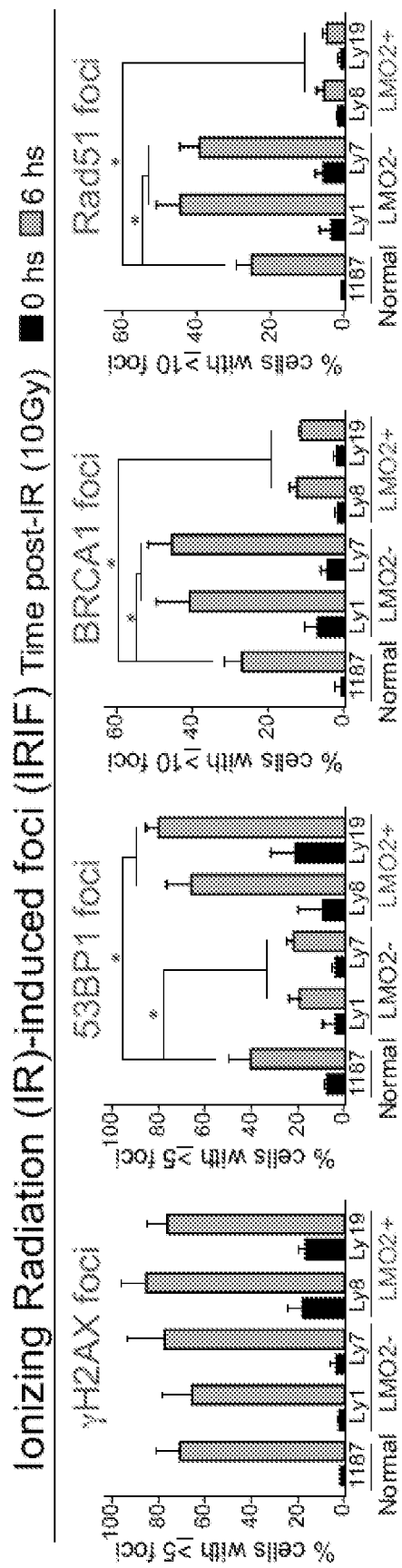

To determine whether LMO2 plays a role in DNA repair, human DLBCL cells expressing different LMO2 protein levels were utilized. Based on immunoblot results, DLBCL cells were classified as having low or high LMO2 levels (DLBCL$^{LMO2-}$ and DLBCL$^{LMO2+}$ respectively) (FIG. 1A). A human Epstein Barr-Virus (EBV)-immortalized lymphoblast cell line (HCC1187, ATCC) was used to determine normal LMO2 expression and T cell-derived non-LMO2-expressing Jurkat cells were used as the negative control (FIG. 1A). Next, the presence of core factors for the NHEJ (53BP1 protein) and HR (Rad51 protein) pathways at DSBs produced by ionizing radiation (IR)-induced foci (IRIF) were evaluated by immunofluorescence. In these studies, the phosphorylated form of histone H2AX (γH2AX) is used as an IRIF marker. All DLBCL cell lines and lymphoblast cells studied exhibited a similar increase in γH2AX IRIF, showing that the recognition of IR-induced DSBs is not affected by LMO2 cellular concentrations (FIG. 1B). DLBCL$^{LMO2+}$ cells showed a significant decrease in the number of BRCA1 and Rad51 IRIF when compared to DLBCL$^{LMO2-}$ and control lymphoblast cells (FIG. 1B). The defects observed in DLBCL$^{LMO2+}$ cells were not due to low BRCA1 or Rad51 protein expression (FIG. 1C), or variations in cell-cycle distribution as the percentage of cycling cells was equivalent in all genotypes tested (FIG. 1D). Since BRCA1 and Rad51 are core proteins of the HR pathway, it was concluded that DLBCL$^{LMO2+}$ cells are deficient in HR-dependent DSB repair, probably due to the observed high LMO2 protein levels. In support of this, shRNA-mediated LMO2 knockdown in DLBCL$^{LMO2+}$ cells increased numbers of both BRCA1 and Rad51 IRIF to levels similar to control cells. In addition, LMO2 expression in DLBCL$^{LMO2-}$ cells decreased the number of BRCA1 and Rad51 IRIF (FIG. 1E). Interestingly, DLBCL$^{LMO2+}$ cells showed higher basal γH2AX levels when compared to DLBCL$^{LMO2-}$ and lymphoblast cells via immunofluorescence (FIG. 1B). This increase in DSBs in DLBCL$^{LMO2+}$ cells is most probably due to an impaired HR pathway, which is crucial DNA replication-associated DSB repair (Andreassen and D'Andrea, Carcinogenesis 27, 883-892 (2006); Sonoda et al., The EMBO journal 17, 598-608 (1998)). In support of this, expression of LMO2 protein in LMO2-negative OCI-Ly1 cells induced the accumulation of DSBs as visualized via γH2AX staining and chromatid as well as chromosome breaks in metaphase spreads (FIG. 1F). A similar decrease in the number of BRCA1 and Rad51 damage foci was observed in DLBCL$^{LMO2+}$ cells exposed to topoisomerase II inhibitor doxorubicin, the main genotoxic agent used for the treatment of DLBCL (Habermann et al., Journal of clinical oncology 24, 3121-3127 (2006)) (FIG. 1G). These data show that LMO2 expression affects repair of DSBs produced by different genotoxic agents.

LMO2-overexpressing human osteosarcoma U2OS cells (referred to as U2OSLMO2+ cells, unless otherwise noted) showed a similar deficiency in BRCA1 and Rad51 TRW (FIG. 1H). Altogether, these data showed that LMO2 inhibits HR activity. Further, the LMO2-dependent HR inhibition is also observed in non-lymphoid cells, suggesting that LMO2 may regulate HR in most cell types.

Example 3: LMO2 is a Novel 53BP1-Associated Factor During DSB Repair

Next, the behavior of NHEJ proteins after DNA damage was evaluated in the same DLBCL cell lines and found that DLBCL$^{LMO2+}$ cells displayed significantly increased numbers of 53BP1 IRIF when compared to control cells (FIG. 1B). This suggested that LMO2 may play a role in 53BP1 complex stability at DSBs. In support of this observation, it was found that LMO2 presence at DSB sites was 53BP1-dependent, as 53BP1 depletion significantly decreased LMO2 and γH2AX co-localization (FIG. 2A). Finally, further studies showed that LMO2 and 53BP1, as well as 53BP1-interacting protein RIF1, co-immunoprecipitate after IR exposure (FIG. 2B). Noteworthy, 53BP1 and LMO2 showed a weak interaction in non-irradiated cells probably due to the increased DNA damage observed in cells expressing LMO2 protein (FIG. 1G). Immunoprecipitation assays with antibodies against 53BP1 confirmed the interaction with LMO2, which increased after exposure to ionizing radiation. Based on these data, it was concluded that LMO2 forms a complex with 53BP1 after DNA damage and that LMO2 plays an important and specific role in the choice between NHEJ and HR pathways for DSB repair.

Example 4: LMO2-Mediated HR Inhibition Depends on 53BP1

Figure 2C:
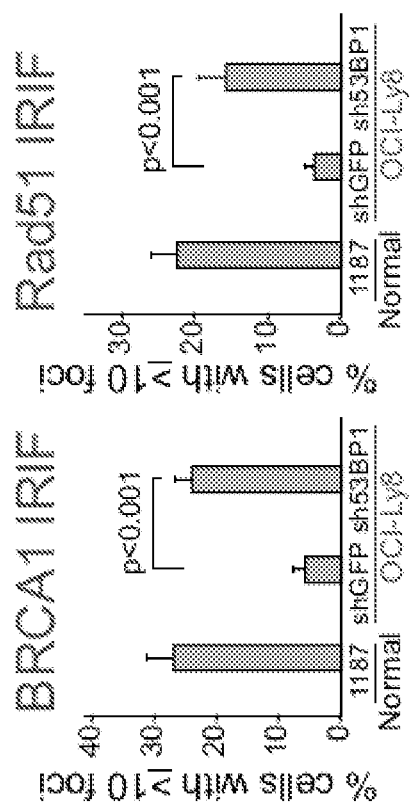

As LMO2 expression decreases BRCA1 and Rad51 IRIF and interacts with 53BP1 complex, an HR inhibitor, experiments were performed to determine whether 53BP1 knockdown rescued the BRCA1 and Rad51 defects observed in LMO2+ cells. 53BP1 deficiency was found to increase the number of BRCA1 and Rad51 IRIF when compared to control shGFP cells (FIG. 2C). These data revealed that LMO2-mediated HR inhibition is 53BP1-dependent. Moreover, the data demonstrated that LMO2 does not affect the expression of essential HR factors as DLBCL$^{LMO2+}$ cells possess a functional HR pathway.

Example 5: LMO2 Inhibits HR in G1 Phase

Based on the preceding data, it was hypothesized that LMO2 is a major negative regulator of the HR pathway. In support of this, DLBCL$^{LMO2-}$ cells exposed to IR showed HR activity in G1 phase. Indeed, using cyclin A expression to mark S and G2 phases, DLBCL$^{LMO2-}$ cells were found to form BRCA1 IRIF in the G1 phase (cyclin A-negative cells, see FIG. 3A). No BRCA1 IRIF were observed in G1 for DLBCL$^{LMO2+}$ or lymphoblast cells (FIG. 3A). Similar results were observed when analyzing U2OS cells after CRISPR/Cas9-mediated LMO2 deletion (LMO2ΔU2OS cells). Indeed, LMO2AU2OS cells showed a significant G1-associated increase in BRCA1 IRIF when compared to control U2OS cells (FIG. 3B). Moreover, as a measure of HR activity, sister chromatid exchanges (SCEs) were monitored, which are Rad51 activity-dependent (Sonoda et al., The EMBO journal 17, 598-608 (1998)). Using HCC1187 lymphoblasts as control, it was found that DLBCL$^{LMO2-}$ cells exhibit a high frequency of SCE (FIG. 3C). Contrarily, DLBCL$^{LMO2+}$ cells had very low SCE frequency relative to lymphoblast cells (FIG. 3C). Furthermore, LMO2 overexpression in DLBCL$^{LMO2-}$ cells decreased SCE frequency as well as BRCA1 foci in G1 cells to that of control cells (FIGS. 3A and 3C). These data show that HR activity depends on cellular LMO2 levels. Altogether, it was concluded that LMO2 is essential for inhibiting HR-mediated DSB repair in the G1 phase and that LMO2 is a major determinant of DSB repair pathway choice. Consequently, when LMO2 is highly expressed, as in DLBCL$^{LMO2+}$ cells, it can also inhibit HR-dependent DSB repair in S/G2 phases.

Figure 4A:
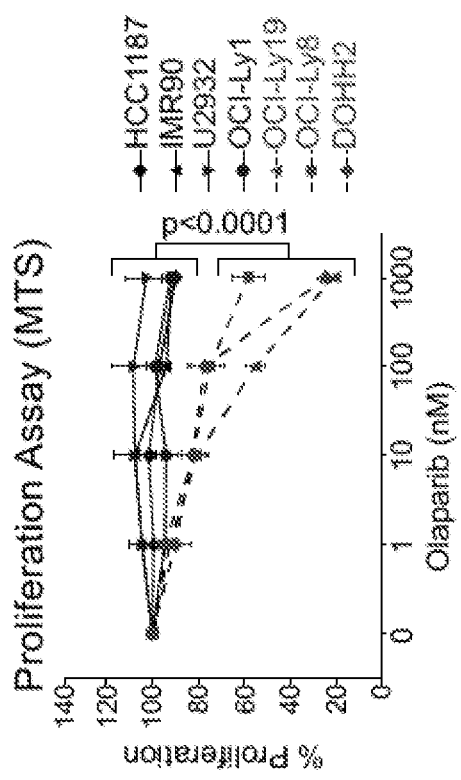
FIGS. 4A-4F: PARP inhibitor olaparib induces cell apoptosis and decreases proliferation of lymphoma cells.
Figure 4B:
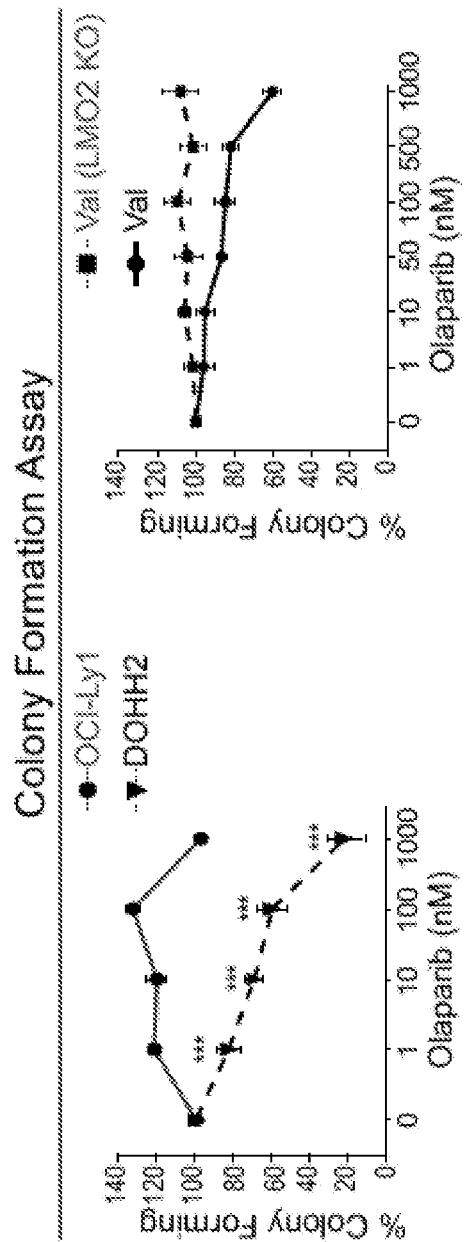
Figure 4D:
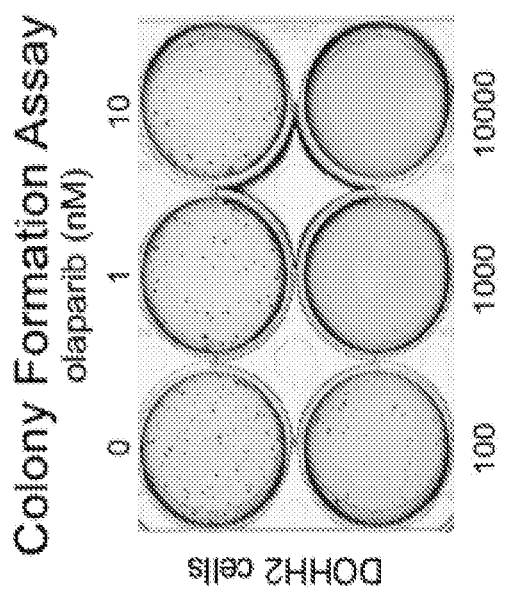
Figure 4C:
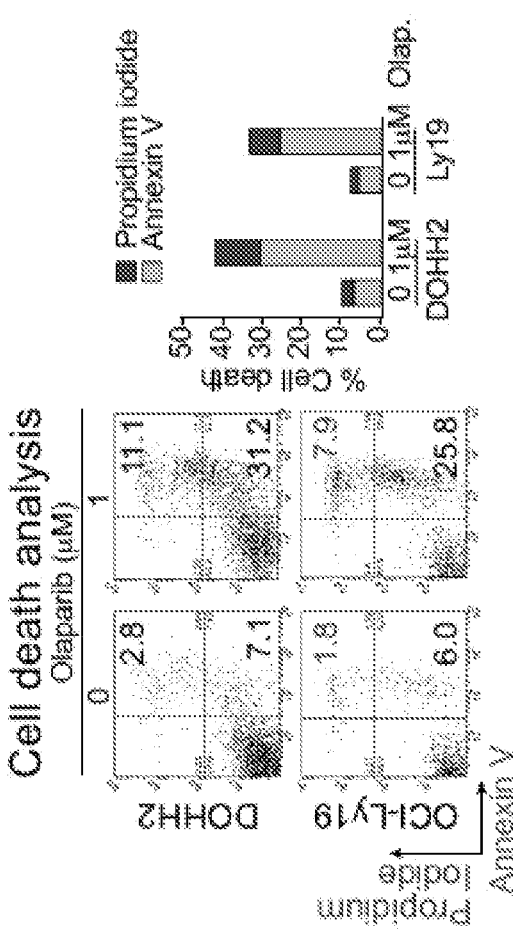
Figure 4E:
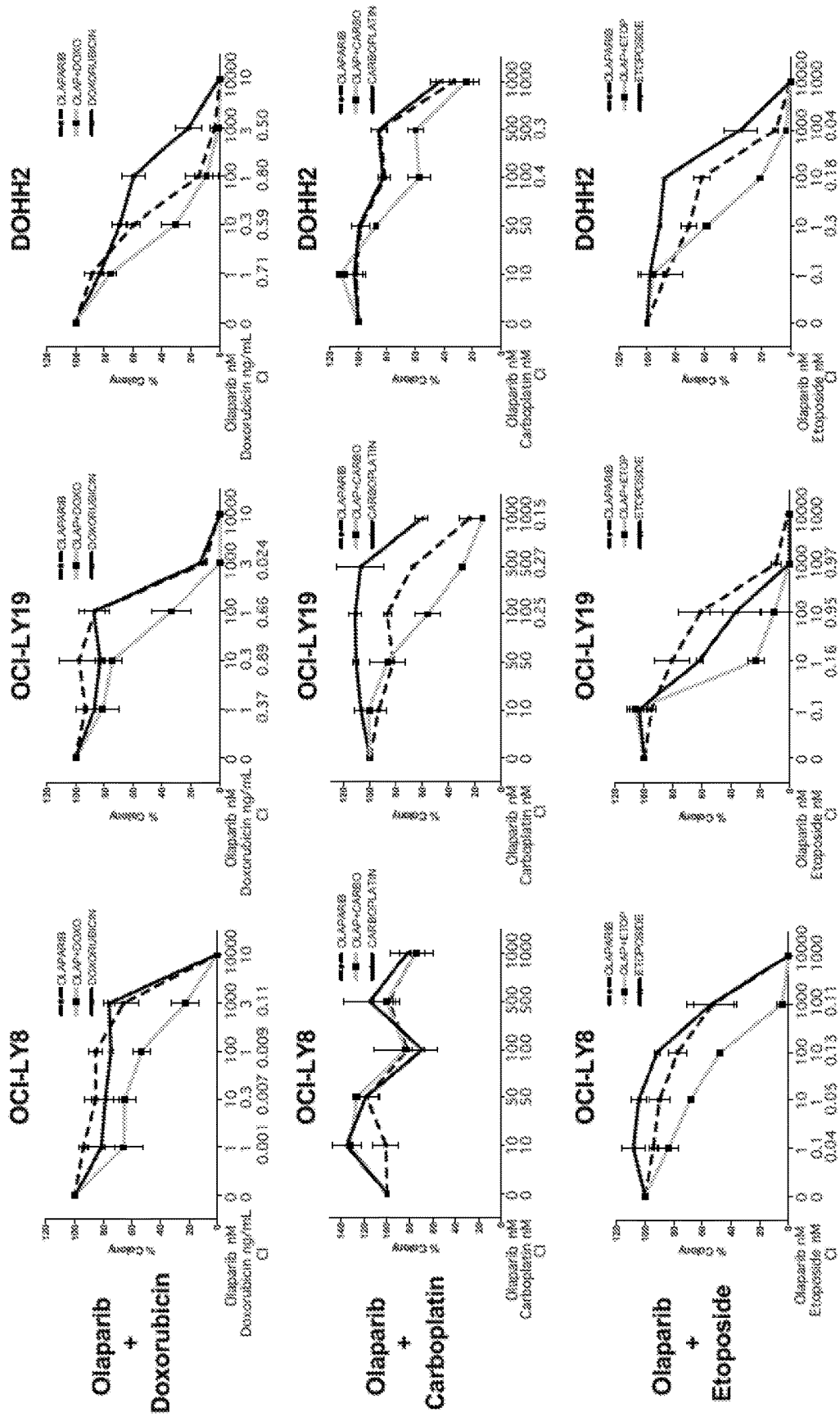
Figure 4E:
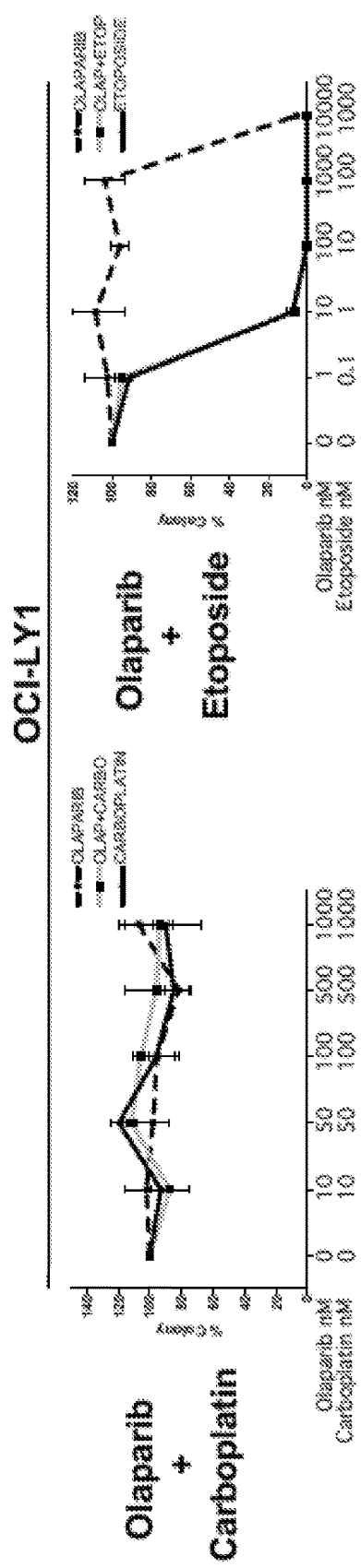
Figure 4F:
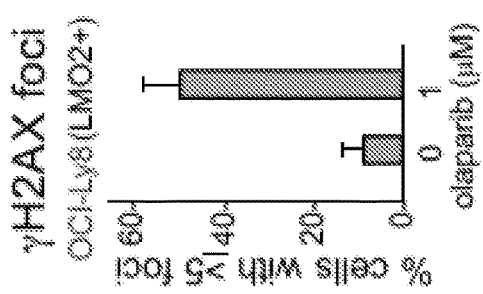

Example 6: The PARP1/2 Inhibitor Olaparib Induces DNA Damage and a Proliferation Defect in DLBCL$^{LMO2+}$ Cells In Vitro HR-deficient cells are sensitive to inhibitors of the single-stranded DNA repair protein poly(ADP-ribose) polymerases (PARP) 1 and 2 (Farmer et al., Nature 434, 917-921 (2005); Bryant. et al., Nature 434, 913-917 (2005); Jackson and Bartek, Nature 461, 1071-1078 (2009)). Mechanistically, loss of PARP1/2 activity decreases the repair efficiency of single-stranded DNA breaks, which are then converted into DSBs during DNA replication. Dividing cells can repair these DSBs via Rad51-dependent HR using the sister chromatid as a template. Hence, PARP1/2 inhibition is particularly toxic in BRCA1- or BRCA2-deficient cells, which are HR defective. The ability of PARP1/2 inhibitors (PARPi) to selectively kill HR-deficient cells is used in treatment of breast and ovarian cancers where Brca1 or Brca2 is mutated (Fong et al., NEJM 361, 123-134 (2009); Jackson and Bartek, Nature 461, 1071-1078 (2009)). To determine the effect of LMO2-dependent inhibition of HR, DLBCL$^{LMO2+}$, DLBCL$^{LMO2-}$ and control cells were challenged with an inhibitor of PARP1/2 (PARPi; olaparib). This drug has been shown to cause high levels of genomic instability and a cell proliferation defect in BRCA1-deficient cells (Farmer et al., Nature 434, 917-921 (2005)). Thus, olaparib's effects on proliferation, colony formation, apoptosis and cell death were examined. In comparison to human primary lung fibroblasts (IMR90) and EBV-transduced normal human lymphoblasts (HCC1187), which express normal LMO2 levels, and two DLBCL$^{LMO2-}$ cell lines (OCI-Ly1 and U2932, FIG. 1A), olaparib induced a statistically significant ($p<0.001$ by ANOVA) decrease in cell proliferation in all three DLBCL$^{LMO2+}$ cell lines, (OCI-Ly8, OCI-Ly19 and DOHH2 in FIG. 4A). Noteworthy, these DLBCL$^{LMO2+}$ cell lines are double-hit DLBCLs (Drexler et al., Leuk Lymphoma 57, 1015-1020 (2016)) for which currently there is no effective treatment available (Dunleavy K J, Oncol Pract 12, 241-242 (2016); Petrich et al., Blood 124, 2354-2361 (2014)). Concordantly, a pronounced olaparib-mediated decrease in colony formation and increased cell death via apoptosis in DLBCL$^{LMO2+}$ cell lines was observed (FIGS. 4B, 4C, 4D and 4E), while there was no or minimal effect on DLBCL$^{LMO2-}$ and control cell lines (FIG. 4A). The IC50 values of olaparib in analyzed DLBCL$^{LMO2+}$ cell lines were markedly lower than the 2 µM that was observed in the blood of breast cancer treated patients (Ashworth A A, Journal of clinical oncology 26, 3785-3790 (2008)). Indeed, olaparib IC50 values were: 0.8 µM for OCI-Ly8, 0.13 µM for OCI-19, and 0.12 µM for DOHH2. Further, the observed effects on proliferation, apoptosis and colony formations were similar or larger than the effects previously reported in breast and ovarian cell lines with similar concentrations of olaparib (Pierce et al., Cancer Biol Ther 14, 537-545 (2013); Stordal et al., Mol Oncol 7, 567-579 (2013); Shimo et al., Breast Cancer 21, 75-85 (2014)). This proliferation defect in DLBCL$^{LMO2+}$ cells is most probably due to the increased DNA damage observed after exposure to PARPi (FIG. 4F). Remarkably, preliminary studies in these three DLBCL cell lines demonstrated that these effects of olaparib are synergistic with doxorubicin, the main chemotherapy drug used for upfront treatment of DLBCL patients (Habermann et al., Journal of clinical oncology 24, 3121-3127 (2006); Coiffier et al., NEJM 346, 235-242 (2002)) (FIG. 4E). Although not at the same degree, carboplatin (OCI-Ly19 and DOHH2) and etoposide also showed synergy with olaparib (FIG. 4E). These results support a model where LMO2 inhibits BRCA1-dependent DNA repair in DLBCL$^{LMO2+}$ cells and increases their sensitivity to olaparib, inducing synthetic lethality that can be further potentiated by standard chemotherapy.

Example 7: the PARP1/2 Inhibitor Olaparib Slows Growth of DLBCL$^{LMO2+}$ Cells In Vivo To examine if the effect of olaparib on cell viability can also be observed in vivo, we used DLBCL xenograft models.

Groups of non-obese diabetic/severe combined immunodeficiency (NOD/SCID) mice were subcutaneously inoculated with LMO2 negative DLBCL cell line OCI-Ly1 or LMO2 positive DLBCL cell line OCI-Ly19. In these experiments, olaparib increased the lifespan of OCI-Ly19 xenografts when compared with the control group (FIG. 5A). However, in OCI-Ly1 xenografts olaparib did not produce any effect (FIG. 5A). The increased lifespan produced by the exposure to olaparib correlates with an increase in cell death in OCI-Ly19 tumors as evaluated via Annexin V, propidium iodide (PI) and Tunnel assay (FIGS. 5B and 5C). Moreover, olaparib also increased the life-span of OCI-Ly19 tumors exposed to RCHOP (FIG. 5A). This is in agreement with the synergy previously observed between olaparib and doxorubicin (main genotoxic agent in RCHOP therapy) in in vitro assays (FIG. 4E).

Figure 6A:
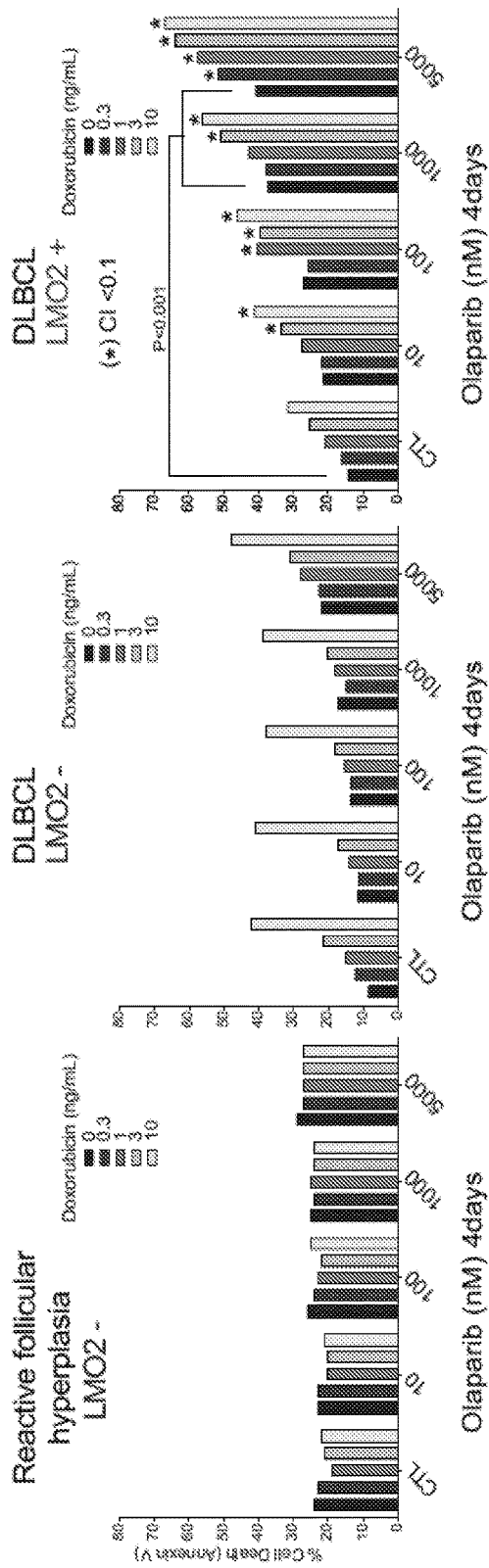
FIGS. 6A-6C: Olaparib and doxorubicin show synergy to kill primary DLBCL cells expressing LMO2.
Figure 6C:
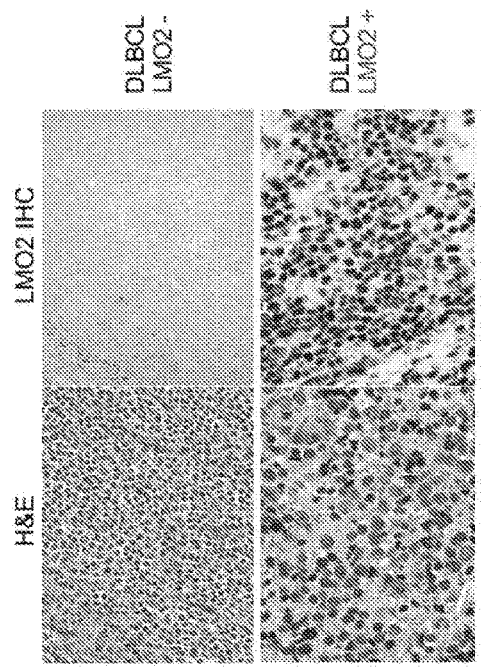
Figure 6B:
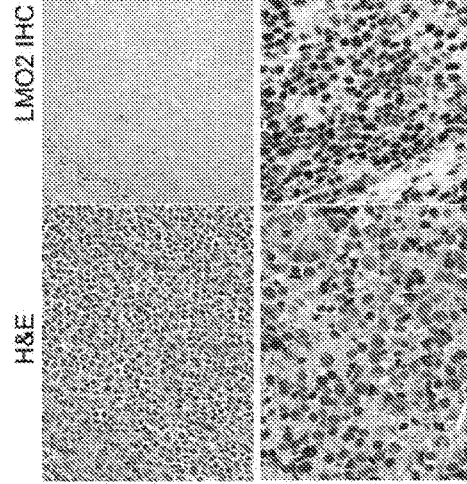

Example 8: The PARP1/2 Inhibitor Olaparib and Genotoxic Agent Doxorubicin Show Synergy in Killing a Primary DLBCL Tumor Expressing LMO2 but not in LMO2 Negative Tumors It was determined whether olaparib alone or in combination with doxorubicin also shows an effect on primary human tumor sample viability depending on the LMO2 protein expression level. As shown in FIG. 6A, olaparib alone and in combination with doxorubicin only affected the proliferation capacity of the DLBCL sample expressing LMO2 protein, as evaluated via Western blotting and IHC (FIGS. 6B and 6C). These results demonstrate that the expression of LMO2 protein (LMO2+) sensitizes the tumors to PARP1/2 inhibitors and that this effect can be enhanced when combined with other genotoxic agents.

Figures 7A, 7B:
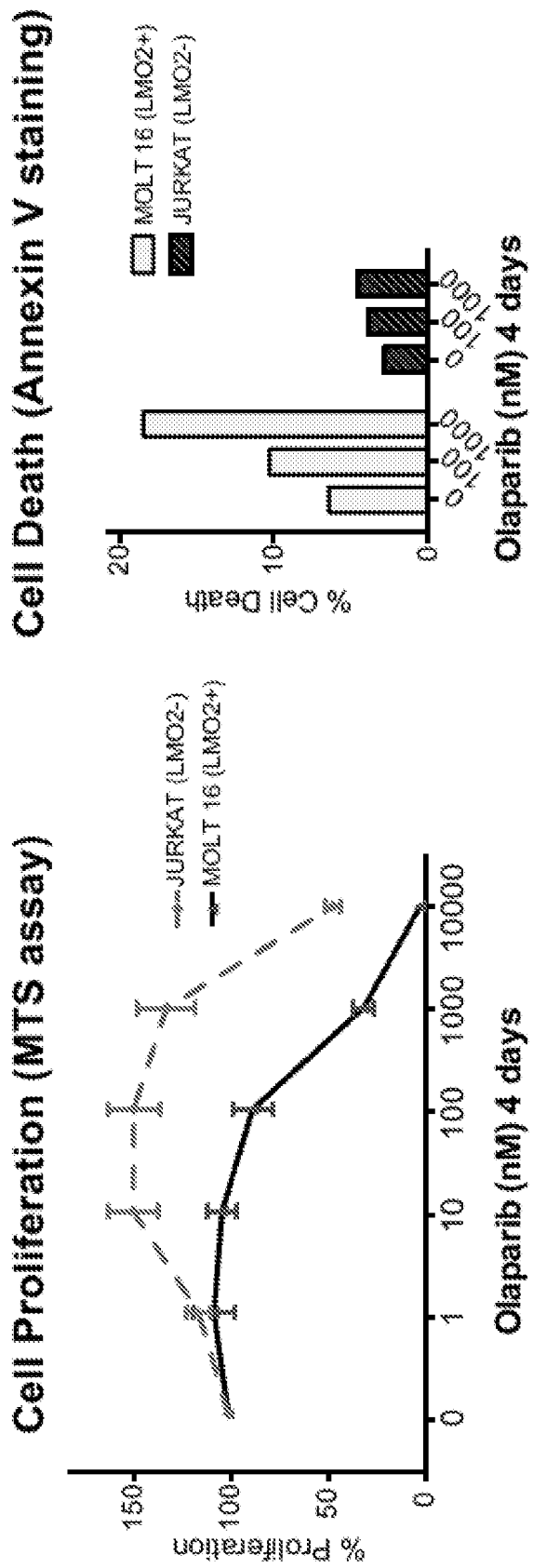
FIGS. 7A-B. PARP inhibitor olaparib induces cell apoptosis and decreases proliferation of T lymphoblastic leukemia cells.

Example 9: The PARP1/2 Inhibitor Olaparib Induces a Proliferation Defect and Cell Death in T-ALL LMO2 Positive Cells In Vitro LMO2 is a known oncogene implicated in the pathogenesis of T-cell acute lymphoblastic leukemia (T-ALL). To extend out studies in DLBCL to T-ALL, we assessed olaparib's effects on cell proliferation, apoptosis and cell death in T-ALL cell lines MOLT16 (LMO2-positive) and Jurkat (LMO2-negative). Olaparib induced a statistically significant ($p<0.001$ by ANOVA) decrease in cell proliferation (FIG. 7A) and an increase in cell death (FIG. 7B) in LMO2 expressing versus LMO2 negative T-ALL cell line.

What is claimed:

1. A method of treating a lymphoproliferative disorder with a defective homologous recombination DNA repair in a mammalian patient in need thereof, the method comprising:
   a) measuring a homologous recombination DNA repair marker selected from LIM domain only 2 (LMO2) in B-lymphocytes isolated from a mammalian subject suffering from a lymphoproliferative disorder and detecting an increase in the level of LMO2 compared to LMO2 level in B-lymphocytes from a mammal of the same species as the mammalian subject that is not suffering from a lymphoproliferative disorder to identify the mammalian patient; and b) administering an effective amount of Poly (ADP-ribose) polymerase (PARP) 1/2 inhibitor to the mammalian patient.

2. The method of claim 1, wherein the lymphoproliferative disorder is lymphoma.

3. The method of claim 1, wherein the lymphoproliferative disorder is diffuse large B cell lymphoma (DLBCL), germinal center B cell-like diffuse large B cell lymphoma (GCB), activated B cell-like diffuse large B cell lymphoma (ABC), primary mediastinal B cell lymphoma (PMBL), double-hit lymphoma (DHL), follicular lymphoma (FL), Burkitt lymphoma (BL), mantle cell lymphoma (MCL), small cell lymphocytic lymphoma (SLL), mucosa-associated lymphoid tissue lymphoma (MALT), splenic marginal zone lymphoma (SMZL), nodal marginal zone lymphoma (NMZ), lymphoplasmacytic lymphoma (LPL), post-transplant lymphoproliferative disorder (PTLD), lymphoblastic lymphoma (LBL), B and T-cell acute lymphoblastic leukemia (B ALL and T-ALL), double hit diffuse large B cell lymphoma, or multiple myeloma.

4. The method of claim 1, wherein increased LMO2 is detected in 30% or more of malignant-B-lymphocytes present in a tumor biopsy from the mammalian patient.

5. The method of claim 1, wherein the mammalian patient has malignant B-lymphocytes, and the LMO2 level in the malignant-B-lymphocytes is higher than the level of LMO2 observed in human Epstein Barr-Virus (EBV)-immortalized lymphoblast cell line (HCC1187, ATCC).

6. A method of treating acute lymphoblastic leukemia with a defective homologous recombination DNA repair in a mammalian patient in need thereof, the method comprising:
a) measuring a homologous recombination DNA repair marker selected from LIM domain only 2 (LMO2) in lymphocytes isolated from a mammalian subject suffering from acute lymphoblastic leukemia and detecting an increase in the level of LMO2 compared to LMO2 level in lymphocytes from a mammal of the same species as the mammalian subject that is not suffering from acute lymphoblastic leukemia to identify the mammalian patient;
b) administering an effective amount of Poly (ADP-ribose) polymerase (PARP) 1/2 inhibitor to the mammalian patient.

7. The method of claim 6, wherein acute lymphoblastic leukemia (ALL) is B-cell ALL or T-cell ALL.

8. The method of claim 6, wherein LMO2 is detected in 30% or more of malignant B-lymphocytes or T-lymphocytes present in a tumor biopsy from the mammalian patient.

9. The method of claim 6, wherein the LMO2 level in malignant B-lymphocytes or T-lymphocytes from the mammalian patient is higher than the level of LMO2 observed in human Epstein Barr-Virus (EBV)-immortalized lymphoblast cell line (HCC1187, ATCC).

10. The method of claim 1, wherein step (a) comprises measuring LMO2 protein levels.

11. The method of claim 10, wherein LMO2 protein levels is are measured by immunohistochemistry (IHC), flow cytometry or Western blotting.

12. The method of claim 1, wherein the PARP 1/2 inhibitor is olaparib, veliparib, iniparib, rucaparib, niraparib, talazoparib, CEP-9722, or INO-1001.

13. The method of claim 12, wherein the PARP 1/2 inhibitor is administered at a dose between 1 to 1000 mg/kg.

14. The method of claim 1, wherein administration of the PARP 1/2 inhibitor reduces tumor volume or tumor burden in the mammalian patient.

15. The method of claim 1, wherein the mammalian patient has a relapsed lymphoproliferative disorder and is treated with the PARP 1/2 inhibitor without administration of a second chemotherapeutic agent.

16. The method of claim 1, wherein the mammalian patient has a newly diagnosed lymphoproliferative disorder and step (b) further comprises administering a second chemotherapeutic agent or combination of agents to the mammalian patient.

17. The method of claim 16, wherein the second chemotherapeutic agent or combination of agents is doxorubicin, cisplatin, bleomycin, vinblastine, dacarbazine, etoposide, cyclophosphamide, vincristine, procarbazine, prednisolone, carmustine, cytarabine, melphalan, CHOP (cyclophosphamide, doxorubicin, vincristine, and prednisone), COPP (cyclophosphamide, vincristin, procarbazine, and prednisone), CVP (cyclophosphamide, vincristine, and prednisone), EPOCH (etoposide, prednisone, vincristine, cyclophosphamide, and hydroxydaunorubicin), Hyper-CVAD (hyperfractionated cyclophosphamide, vincristine, adriamycin, and dexamethasone), ICE (iosfamide, carboplatin, and etoposide), R-CHOP (cyclophosphamide, doxorubicin, prednisone, rituximab, and vincristine), R-CVP (rituximab, cyclophosphamide, vincristine, and prednisone), R-EPOCH (rituximab, etoposide, prednisone, vincristine, cyclophosphamide, and hydroxydaunorubicin), or R-ICE rituximab ifosfamide, carboplatin, and etoposide), R-DHAP (rituximab, dexamethasone, cytarabine, and cisplatin), McGrath protocol or myeloablative regimens or further in combination with other antibodies directed to CD20 or other surface proteins expressed by B-cell tumors.

18. The method of claim 1, wherein the mammalian subject is a human subject.

19. The method of claim 2, wherein increased LMO2 is detected in 30% or more of malignant-B-lymphocytes present in a tumor biopsy from the mammalian patient.

20. The method of claim 12, wherein increased LMO2 is detected in 30% or more of malignant-B-lymphocytes present in a tumor biopsy from the mammalian patient.

21. The method of claim 15, wherein increased LMO2 is detected in 30% or more of malignant-B-lymphocytes present in a tumor biopsy from the mammalian patient.

22. The method of claim 16, wherein increased LMO2 is detected in 30% or more of malignant-B-lymphocytes present in a tumor biopsy from the mammalian patient.

* * * * *

SEQUENCE LISTING

```
<160> NUMBER OF SEQ ID NOS: 2

<210> SEQ ID NO 1
<211> LENGTH: 1630
<212> TYPE: DNA
<213> ORGANISM: Homo sapiens
<220> FEATURE:
<221> NAME/KEY: misc_feature
<223> OTHER INFORMATION: Homo sapiens LIM domain only 2 (rhombotin-like
      1), mRNA
<300> PUBLICATION INFORMATION:
<308> DATABASE ACCESSION NUMBER: BC035607.1
<309> DATABASE ENTRY DATE: 2003-10-07
<313> RELEVANT RESIDUES IN SEQ ID NO: (1)..(1630)

<400> SEQUENCE: 1
gaaggttaag tcctgagcag cagcagcagc tgcagccgcc tggagccagg ctgcgcgccc      60
cggcccccgc ctcggccgcg gcgcgcccgc agcccggtga ttcgctctct ctctttggcg     120
tttgaaggga gcgcggtgac tgtccttgag cgcggagggg cgagctcgcc ggcggagcgc     180
cggagcaagc ggaggcgcag gagcggcggc gacggcggcg gcggcggcgg cgcccgagca     240
cccgaggggg tccgagcccc ggcagccggc cagccccgcg ccacaaaggg agcgccccg      300 ccgcccggca ccccgcctcc ctccccaatg tcctcggcca tcgaaaggaa gagcctggac     360
ccttcagagg aaccagtgga tgaggtgctg cagatccccc catccctgct gacatgcggc     420
ggctgccagc agaacattgg ggaccgctac ttcctgaagg ccatcgacca gtactggcac     480
gaggactgcc tgagctgcga cctctgtggc tgccggctgg gtgaggtggg gcggcgcctc     540
tactacaaac tgggccggaa gctctgccgg agagactatc tcaggctttt tgggcaagac     600
ggtctctgcg catcctgtga caagcggatt cgtgcctatg agatgacaat gcgggtgaaa     660
gacaaagtgt atcacctgga atgtttcaag tgcgccgcct gtcagaagca tttctgtgta     720
ggtgacagat acctcctcat caactctgac atagtgtgcg aacaggacat ctacgagtgg     780
actaagatca atgggatgat ataggcccga gtccccgggc atctttgggg aggtgttcac     840
tgaagacgcc gtcccatgg catcttcgtc ttcactctta ggcactttgg gggtttgagg     900
gtggggtaag ggatttctta ggggatggta gacctttatt gggtatcaag acatagcatc     960
```

-continued

```
caagtggcat aattcagggg ctgacacttc aaggtgacag aaggaccagc ccttgaggga    1020
gaacttatgg ccacagccca tccatagtaa ctgacatgat tagcagaaga aaggaacatt    1080
taggggcaag caggcgctgt gctatcatga tggaatttca tatctacaga tagagagttg    1140
ttgtgtacag acttgttgtg actttgacgc ttgcgaacta gagatgtgca attgatttct    1200
tttcttcctg gcttttaac tcccctgttt caatcactgt cctccacaca agggaaggac    1260
agaaaggaga gtggccattc ttttttttctt ggccccttc ccaaggcctt aagctttgga    1320
cccaaggaaa actgcatgga gacgcatttc ggttgagaat ggaaaccaca acttttaacc    1380
aaacaattat ttaaagcaat gctgatgaat cactgttttt agacaccttc attttgaggg    1440
gaggagttcc acagattgtt tctatacaaa tataaatctt aaaaagttgt tcaactattt    1500
tattatccta gattatatca aagtatttgt cgtgtgtaga aaaaaaaaac agctctgcag    1560
gcttaataaa aatgacagac tgaaaaaaaa aaaaaaaaaa aaaaaaaaaa aaaaaaaaa    1620 aaaaaaaaaa                                                          1630

<210> SEQ ID NO 2
<211> LENGTH: 158
<212> TYPE: PRT
<213> ORGANISM: Homo sapiens
<220> FEATURE:
<221> NAME/KEY: MISC_FEATURE
<223> OTHER INFORMATION: LMO2
<300> PUBLICATION INFORMATION:
<308> DATABASE ACCESSION NUMBER: AAH35607
<309> DATABASE ENTRY DATE: 2003-10-07
<313> RELEVANT RESIDUES IN SEQ ID NO: (1)..(158)

<400> SEQUENCE: 2

Met Ser Ser Ala Ile Glu Arg Lys Ser Leu Asp Pro Ser Glu Glu Pro
1               5                   10                  15

Val Asp Glu Val Leu Gln Ile Pro Pro Ser Leu Leu Thr Cys Gly Gly
            20                  25                  30

Cys Gln Gln Asn Ile Gly Asp Arg Tyr Phe Leu Lys Ala Ile Asp Gln
        35                  40                  45

Tyr Trp His Glu Asp Cys Leu Ser Cys Asp Leu Cys Gly Cys Arg Leu
    50                  55                  60

Gly Glu Val Gly Arg Arg Leu Tyr Tyr Lys Leu Gly Arg Lys Leu Cys
65                  70                  75                  80

Arg Arg Asp Tyr Leu Arg Leu Phe Gly Gln Asp Gly Leu Cys Ala Ser
                85                  90                  95

Cys Asp Lys Arg Ile Arg Ala Tyr Glu Met Thr Met Arg Val Lys Asp
            100                 105                 110

Lys Val Tyr His Leu Glu Cys Phe Lys Cys Ala Ala Cys Gln Lys His
        115                 120                 125

Phe Cys Val Gly Asp Arg Tyr Leu Leu Ile Asn Ser Asp Ile Val Cys
    130                 135                 140

Glu Gln Asp Ile Tyr Glu Trp Thr Lys Ile Asn Gly Met Ile
145                 150                 155
```